United States Patent
Berkner

(10) Patent No.: US 8,903,477 B2
(45) Date of Patent: Dec. 2, 2014

(54) DEVICE FOR MOBILE ELECTROCARDIOGRAM RECORDING

(76) Inventor: Lior Berkner, Ra'anana (IL)

( * ) Notice: Subject to any disclaimer, the term of this patent is extended or adjusted under 35 U.S.C. 154(b) by 686 days.

(21) Appl. No.: 12/375,561

(22) PCT Filed: Jul. 29, 2007

(86) PCT No.: PCT/IL2007/000947
§ 371 (c)(1),
(2), (4) Date: Jan. 29, 2009

(87) PCT Pub. No.: WO2008/015667
PCT Pub. Date: Feb. 7, 2008

(65) Prior Publication Data
US 2010/0069735 A1    Mar. 18, 2010

Related U.S. Application Data

(60) Provisional application No. 60/820,780, filed on Jul. 29, 2006.

(51) Int. Cl.
| A61B 5/04 | (2006.01) |
|---|---|
| A61B 5/00 | (2006.01) |
| A61B 5/0408 | (2006.01) |
| A61B 5/06 | (2006.01) |
| A61B 5/0402 | (2006.01) |
| A61B 5/0428 | (2006.01) |

(52) U.S. Cl.
CPC ............ *A61B 5/04286* (2013.01); *A61B 5/6831* (2013.01); *A61B 5/04085* (2013.01); *A61B 5/061* (2013.01); *A61B 5/04028* (2013.01); *A61B 5/684* (2013.01)

USPC ............ 600/509; 600/372; 600/382; 600/508

(58) Field of Classification Search
CPC ............ A61B 5/0402; A61B 5/04028; A61B 5/6831; A61B 5/684
USPC .......................... 600/382, 508–510, 386–393
See application file for complete search history.

(56) References Cited

U.S. PATENT DOCUMENTS

| 4,353,372 | A | * | 10/1982 | Ayer | 600/393 |
|---|---|---|---|---|---|
| 4,858,617 | A | * | 8/1989 | Sanders | 600/509 |
| 4,889,134 | A | * | 12/1989 | Greenwold et al. | 600/509 |

(Continued)

FOREIGN PATENT DOCUMENTS

RS    WO 01/70105    *   3/2001    ............... A61B 5/00

OTHER PUBLICATIONS

Feldman et al., Charles L. , "Comparison of the Five-Electrode-Derived EASI Electrocardiogram to the Mason Likar Electrocardiogram in the Prehospital Setting", (www.AJConline.org) The American Journal of Cardiology (2005) 96(3):453-456.

(Continued)

*Primary Examiner* — Linda Dvorak
*Assistant Examiner* — Brian M Antiskay

(57) ABSTRACT

A device, system and method for obtaining a 12 lead electrocardiogram (ECG) from measurements obtained with 3 electrodes in some embodiments (it should be noted that some separate embodiments of the present invention relate to such measurements with 4 electrodes). Optionally and preferably, the device, system and method of the present invention may be easily and accurately operated by a layperson.

14 Claims, 11 Drawing Sheets

(56) References Cited

U.S. PATENT DOCUMENTS

| | | | | |
|---|---|---|---|---|
| 4,981,141 A | * | 1/1991 | Segalowitz | 600/509 |
| 6,052,615 A | * | 4/2000 | Feild et al. | 600/509 |
| 6,115,623 A | * | 9/2000 | McFee | 600/372 |
| 6,117,077 A | * | 9/2000 | Del Mar et al. | 600/301 |
| 6,654,631 B1 | * | 11/2003 | Sahai | 600/509 |
| 2003/0073915 A1 | * | 4/2003 | McLeod et al. | 600/509 |
| 2005/0107714 A1 | * | 5/2005 | Matsumura et al. | 600/509 |
| 2007/0232946 A1 | * | 10/2007 | Feild et al. | 600/509 |
| 2008/0312524 A1 | * | 12/2008 | Solosko et al. | 600/393 |
| 2013/0345540 A1 | * | 12/2013 | Salazar et al. | 600/393 |

OTHER PUBLICATIONS

Welinder, MD et al., Annika, "Pediatrics: Diagnostic Conclusions from the EASI-derived 12-lead Electrocardiogram as Compared with the Standard 12-lead Electrocardiogram in Children", American Heart Journal (2006) 151:1059-1064.

Sejersten, MD et al., Maria, "Comparison of EASI-derived 12-lead Electrocardiograms Versus Paramedic-acquired 12-lead Electrocardiograms Using Mason-Likar Limb Lead Configuration in Patients with Chest Pain", Journal of Electrocardiology (2006) 39:13-21.

Jahrsdoerfer, RN et al., Mary, "Clinal Article: Clinical Usefulness of the EASI 12-Lead Continuous Electrocardiographic Monitoring System", Clinical Care Nurse (2005) 25(5):28-38.

American National Standards Institute—"Diagnostic Electrocardiographic Devices", © 2000 by the Association for the Advancement of Medical Instrumentation, ANSI/AAMI EC11:1991/(R)2001.

* cited by examiner

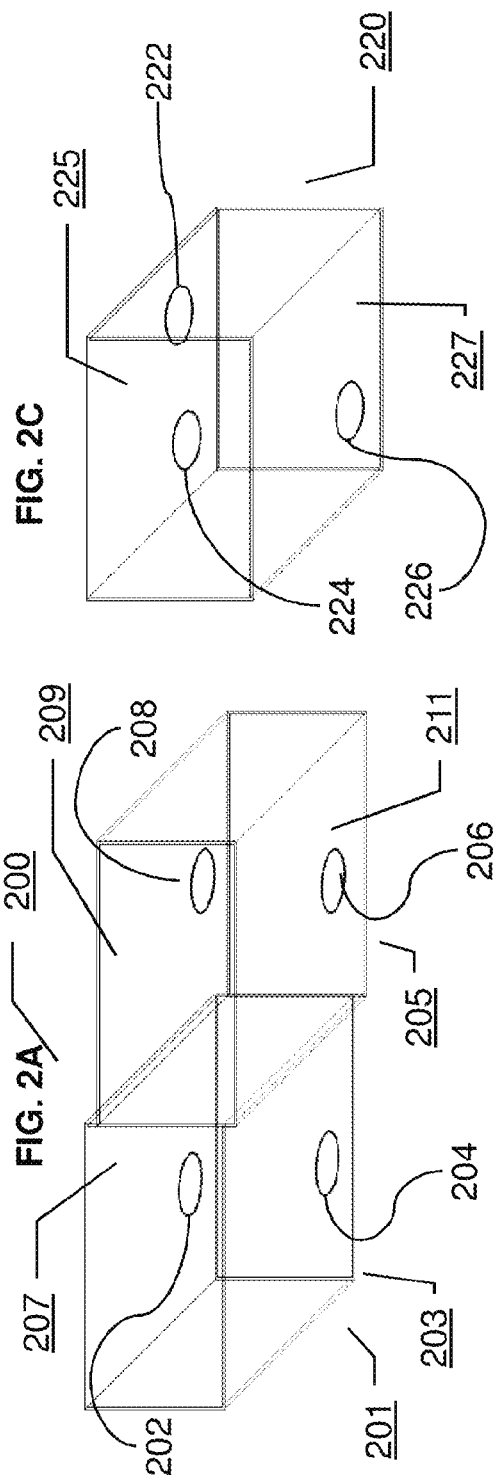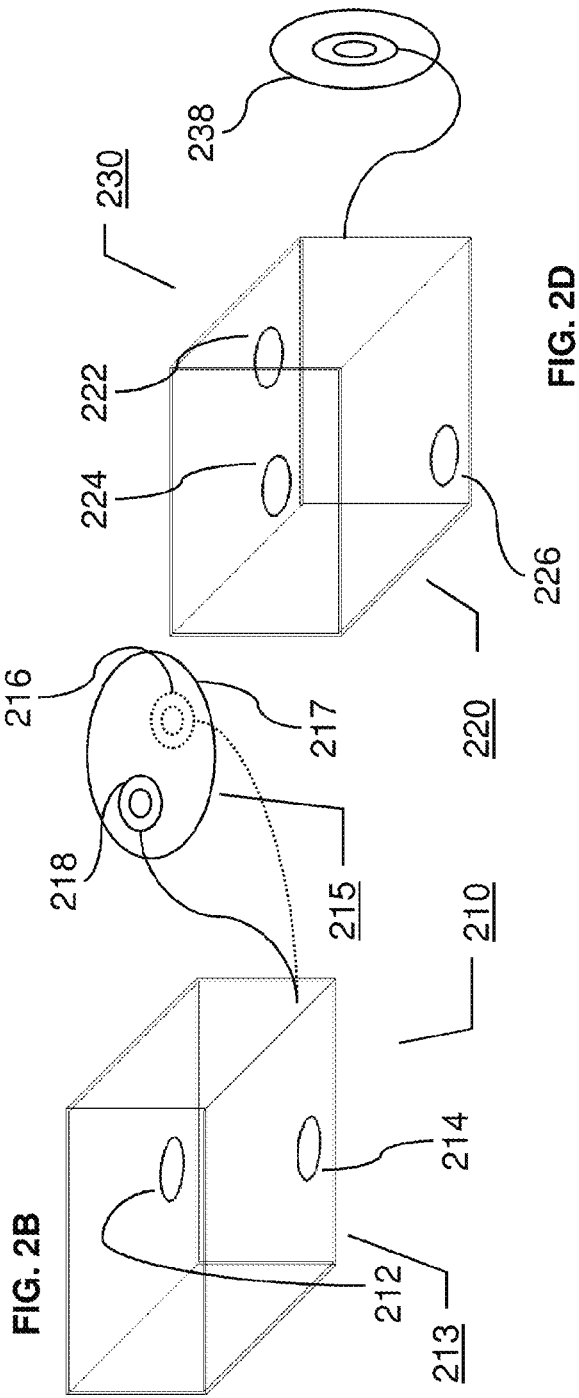

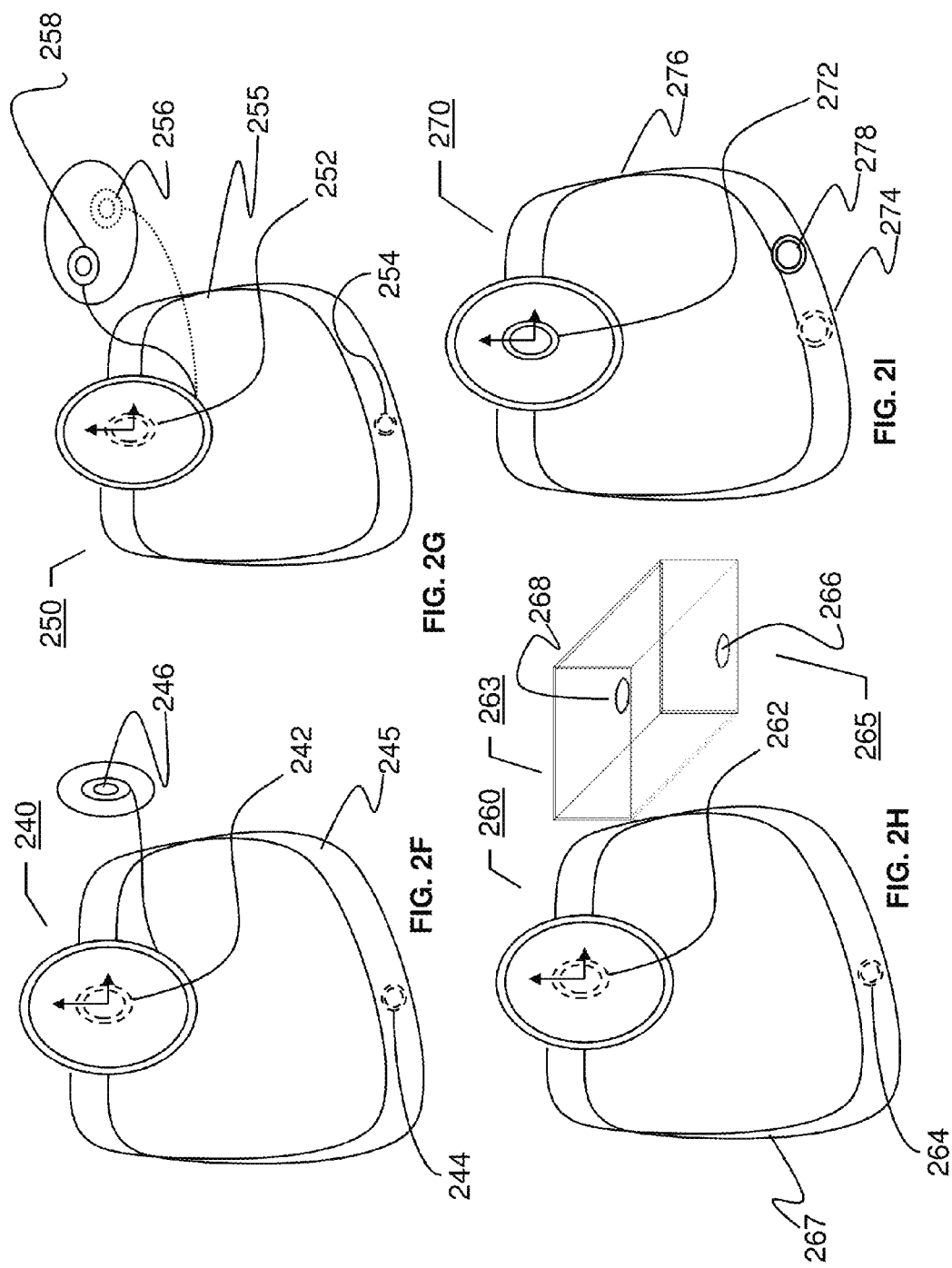

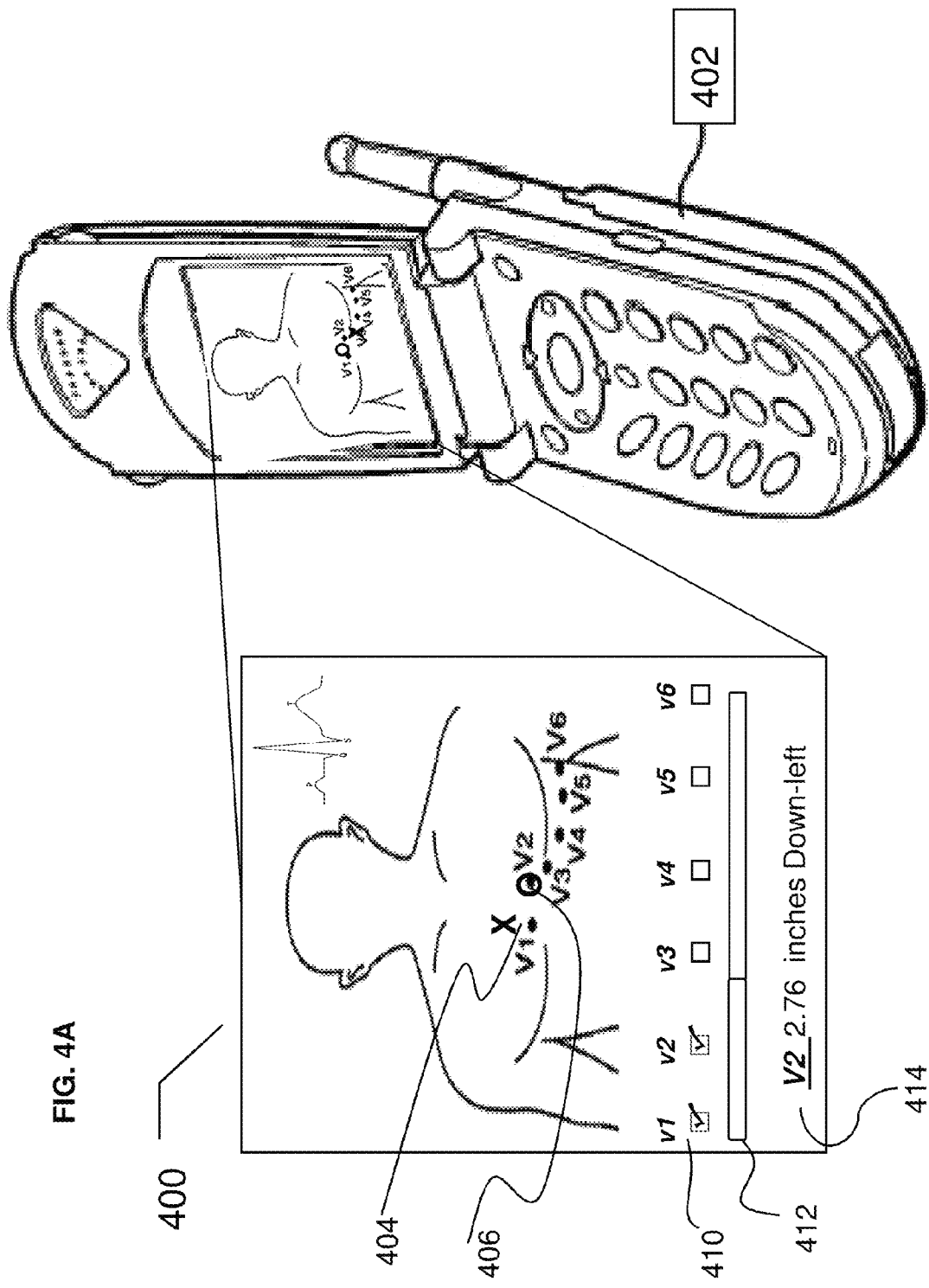

DEVICE FOR MOBILE ELECTROCARDIOGRAM RECORDING

This Application is a national phase of, and claims priority from, PCT Application No. PCT/IL2007/000947, filed on Jul. 29 2007, which claims priority from U.S. Provisional Application No. 60/820,780, filed on Jul. 29 2006, all of which are hereby incorporated by reference as if fully set forth herein.

FIELD OF THE INVENTION

The present invention relates to a device, system and a method for a mobile medical diagnostic equipment and in particular, to such a system and method for an electrocardiogram.

BACKGROUND OF THE INVENTION

Heart problems are one of the leading causes of morbidity and mortality worldwide.

Ischemic heart disease and arrhythmias are the two major types of cardiac abnormalities with prevalence of 12% in the general population, manifested in a wide range of symptoms, most typically chest pain radiating to other parts of the body.

Chest pain is a common symptom occurring in many diseases other than heart disease and since acute ischemic or arrhythmic events can be fatal, a prompt differentiation of the pain's origin could save lives. Ascertaining the symptomatic cardiac origin of the patient's condition can, potentially, shorten the "time to medical consultation" and in turn shorten the "time interval to medical intervention", thereby reducing morbidity and mortality. The indirect results of an accurate diagnosis of a person's condition may prove of great economical value (since an accurate diagnosis may mean fewer hospitalization days, fewer unnecessary trips to the emergency room and so on).

The traditional tool primarily used to detect cardiac events is the Electrocardiogram (ECG). The ECG is a popular tool mainly because it is noninvasive and supplies immediate results (although it also has two major downfalls manifested in its large size, high cost and complexity mainly attributed to the number of wires involved).

Conventionally, when an electrocardiogram of a patient is detected, measured, and recorded in a hospital or a like facility, a total of ten electrodes are attached to the body surface of the patient; namely, six positions for chest leads, and four positions for limb leads. Six limb-lead waveforms (I, II, III, aVR, aVL, and aVF) of standard 12-lead waveforms and six chest-lead waveforms (V1, V2, V3, V4, V5, and V6) of the same are derived from electric potentials of the heart detected and measured by the ten electrodes by measuring means. General measurement positions are shown in FIGS. 1A and 1B, depicting the position used to obtain a 12-lead electrocardiogram.

Such diagnosis and treatment using a plurality of electrodes is possible in a fully-equipped hospital, or the like. However, in an at-home situation it has to date not been possible to obtain a 12 lead ECG using a small device comprising a minimal number of mobile and cordless electrodes, which is easy to use and which will enable detection of heart attack, any time, anywhere and in a low cost.

Mobile ECG units using handheld devices (such as a mobile phone) and telemedicine have been described in the art; however, they collectively do not provide an accurate home use device that could be simply and accurately used by any individual with no need of a prior medical knowledge.

For example US application NO. US2006224071 describes a method off inferring 12 lead ECG from reduced number of electrodes. The electrodes are located at V2 and V5 locations plus at least one electrode positioned substantially level with V5 on the right anterior auxiliary line, and at least one further electrode positioned on each of the right hand side and left hand side of the body. Although requiring a reduced number of electrodes in order to monitor 12 lead ECG, this method does require at least 5 electrodes including one in a non-conventional recording location.

Similarly, PCT Publication WO 2004/038942 to LEE describes a 4 wired electrode recording using a mobile telephone battery pack to detect an ECG. However the application does not indicate which electrode locations are used and does not teach that a full 12 lead ECG may be inferred from the recordings. The electrodes are adhesive, fixed and must be placed in the correct position in order to achieve an accurate reading. In addition, the data is first transmitted to the telephone's battery pack and from there to the telephone itself. Finally, the method described in the above publications requires modifications in the telephone's hardware and software.

US Application Publication No. US2006025695 to WEI describes a method for deriving a 12 lead ECG using a conversion matrix that allows the use of a smaller number of electrodes to predict a 12 lead ECG. However the described device uses 5 electrodes to obtain the 12 lead ECG recording. Furthermore, WEI does not describe a wireless or mobile device that is able to analyze and decipher a 12 lead ECG accurately.

European patent number EP1188412 to Brodnick et al describes an ECG monitor connected to a plurality of lead wires, each lead wire having a transducer capable of receiving an ECG signal from a patient, the ECG monitor having a processor to process the ECG signals from the plurality of lead wires and produce ECG data representative of cardiac condition of the patient, with a wireless communication interface coupled to receive patient ECG data from the ECG monitor and to transmit patient ECG data to a health care provider. Again the issue of mobility is not addressed by Brodnick et al.

German patent number DE10048746 to Tuncay is a device for the receipt and conversion of ECG-signals with three electrodes which are applied to the upper torso of the patient and which are connected via a cable to an A/D converter; however the taught method does not produce a 12 lead ECG which is sufficiently accurate for diagnosis.

German patent number DE19707681 to Erbel et al. relates to a mobile telephone comprising a housing, a transmitter, at least one receiver, a call number memory and buttons located on the housing. The taught device is configured in such a way that at least one emergency call button is mounted on the housing. However it does not teach or suggest obtaining a specific ECG configuration.

SUMMARY OF THE INVENTION

The background art does not teach or suggest a device, system or method for obtaining a 12 lead electrocardiogram (ECG) from measurements obtained with 3 electrodes.

The background art also does not teach or suggest such a device, system or method which may be easily and accurately operated by a layperson (without any substantial medical training).

The background art also does not teach or suggest such a device, system or method which is mobile and which is able to provide results to a remote location, for example to medical personnel located at such a remote location from the subject undergoing the ECG measurements.

The present invention overcomes these disadvantages of the background art by providing a device, system and method for obtaining a 12 lead electrocardiogram (ECG) from measurements obtained with 3 electrodes in some embodiments (it should be noted that some separate embodiments of the present invention relate to such measurements with 4 electrodes). Optionally and preferably, the device, system and method of the present invention may be easily and accurately operated by a layperson. Hereinafter, the term "layperson" refers to any individual without any substantial medical training.

According to preferred embodiments of the present invention, the device is optionally and preferably mobile, and is optionally and more preferably able to provide results of the ECG to a remote location, for example through wireless communication. Most preferably, such results may be provided to medical personnel located at a remote location from the subject undergoing the ECG. Results may optionally include one or more of raw data or processed data.

According to some embodiments, the present invention is of a device able to derive a standard 12-lead electrocardiogram effective for diagnosing a heart condition, in which a minimum number of electrodes (either 3 or 4 electrodes, according to the embodiment of the present invention) are used on the body surface of a living body to thus obtain a comprehensive ECG. Proper positioning of the electrodes is optionally and preferably achieved by utilizing a unique and user friendly navigation system. Optionally and preferably the heart condition may include one or more of ischemic heart disease, acute myocardial infarction, arrhythmias, conduction defects, metabolic disease with heart related effect(s), or the like.

Without wishing to be limited in any way, at least some embodiments of the device of the present invention are able to provide any person (including people with no prior medical knowledge) with the ability to perform "self diagnosis" of ischemic events any time and anywhere, such that the device is preferably a "user friendly" device, more preferably with small scale dimensions.

According to some embodiments of the present invention, the cardio-electric signal is preferably acquired in a consecutive manner from a plurality of electrodes in order to achieve a full 12 lead ECG, unlike background art systems which require simultaneous recording of the electro-cardiac signal. For some embodiments, there is at least one roaming electrode meant to record the V1 to V6 leads. This electrode is preferably moved across the chest so as to enable an in line sampling of the leads (e.g. after the acquisition of the V1 signal with this electrode, the user then preferably moves the electrode to the next V2 location so as to acquire the V2 signal and so on).

For signal acquisition the device of the present invention preferably uses a 3 electrode configuration according to some embodiments, or alternatively may optionally use a 4 electrode configuration embodiment so that a 12 lead ECG is obtained.

According to some embodiments of the present invention which use 4 electrodes, the electrodes are optionally and preferably placed on the user's body as follows: one electrode is in contact with the lower torso or leg; a second electrode is in contact with the left arm (LA); a third electrode is in contact with the right arm (RA) and the fourth electrode is a roaming electrode which is preferably in contact with a plurality of different locations of the user's upper torso, preferably chest (more preferably in a sequential manner). By "upper torso" it is optionally and preferably meant to include "chest". Also it should be noted that where "chest" is stated, unless otherwise noted, it may include "upper torso". By "arm" it is optionally and preferably meant any portion of the upper limb from fingers to the shoulder area.

According to some embodiments, at least one unit is held in the hand and so contacting the arm preferably includes holding a unit in a hand. According to some other embodiments, a unit is held on the wrist (for example with a strap or band, optionally incorporated into a watch or watch-like device), such that at least one electrode contacts the skin of the wrist while at least one other electrode may contact another portion of the body.

According to some embodiments, the device optionally and preferably comprises two subunits. The subunits may optionally be identical. Alternatively, the device components may be split amongst the two subunits.

Preferably each subunit comprises two electrodes optionally located on a different face of the device, such that a first face of the subunit comprises one electrode, while a second face of the subunit comprises the second electrode. Therefore each subunit comprises 2 electrodes on individual faces of the device for a total of 4 electrodes. The electrode on the first face is in contact with at least one body location while the electrode on the second face is in contact with at least one other, different, location. Therefore each subunit is in contact with a plurality of different body recording locations.

The two subunits of the device are preferably used substantially simultaneously or simultaneously to record electrocardiac signals from different locations. For example, the first subunit may optionally be placed at a location that corresponds to location LL or RL (or alternatively lower torso), as depicted in FIG. 1A or 1B. Thus, a first electrode of the first subunit is optionally in contact with one of the legs (or lower torso), while the second electrode on a different face of the first subunit is optionally in contact with the arm, optionally and preferably hand, used to keep the subunit in place at the leg or lower torso location.

The second subunit is optionally sequentially in contact with locations on the upper torso, for example corresponding to the chest (V1 to V6) locations. The second subunit of the device is preferably held to the upper torso with the available free arm (the one not contacting the first subunit). Thus, the RA or LA is optionally in contact with the first electrode on the first face of the second subunit and the second electrode found on the second face of the second subunit is optionally in contact with the chest (locations V1 to V6). Preferably the second face of the second subunit comprising the second electrode is held to the chest while the subunit is gradually moved across the chest, such that the electrode on the second face preferably (and consecutively) contacts a plurality of locations on the chest. In moving the electrode across the chest, each location V1 through to V6 is preferably in contact with the electrode in turn. Combining the signals from locations V1 to V6 with the signals from the other electrodes allows for a calculation of a 12 lead ECG. The device may optionally monitor electro-cardiac signals from all over the upper torso, not necessarily limited only to the traditional V1 to V6 locations, which are given herein for the purpose of illustration only and without intending to be limiting in any way.

According to some embodiments, the second subunit is preferably first placed in contact with a portion of the body other than the upper torso, preferably for example the lower torso or on a leg which is not already being contacted (or has not been contacted) by the first subunit, and is only then placed in contact with the upper torso as described above.

According to other embodiments of the present invention, a 3 electrode configuration is used in order to achieve a 12 lead ECG. Optionally and preferably, the three electrodes are located on a single unit, or alternatively and optionally on two units. The following description is provided with regard to the single unit configuration for the purpose of illustration only and without any intention of being limiting.

At first, the unit is preferably held by the user on one of the lower limbs (or lower torso) so that each of the 3 electrodes is in contact with a different limb. Thus, one electrode is preferably in contact with the left arm; one electrode is preferably in contact with the right arm; and one electrode is preferably in contact with one of the legs or lower torso, in order to calculate the limb leads. After the calculation is completed, the unit is then preferably moved to the user's upper torso in order to calculate the V1 to V6 leads.

Preferably, two electrodes are located on one face of the unit, so that one electrode is in contact with one arm and the other electrode is in contact with the other arm. A second face of the unit preferably includes one electrode (the third electrode) which is preferably initially in contact with the user's lower torso or leg. By placing the electrodes as described above, a recordation of the limb leads is preferably performed. In order to record the precordial limbs, the unit is then preferably moved to the user's upper torso. The hands are still preferably in contact with each of the two electrodes (located on the first face), but the third electrode (located on the second face) is now preferably in contact with the upper torso. By now moving the unit across the chest, each location V1 through to V6 is preferably in contact with the third electrode in turn (again, these locations are given as examples only without any intention of being limiting, as the device may optionally monitor electro-cardiac signals from all over the upper torso area, and is not necessarily limited only to the traditional V1 to V6 locations). Optionally, the potentials monitored from the limb leads may be stored in the device and are then preferably combined with the recorded V1 to V6 locations to further increase the accuracy of the precordial leads calculation.

Optionally and preferably combining the signals from locations V1 to V6 with the signals from the other electrodes as described above permits the calculation of a 12 lead ECG from a device with only three electrodes.

According to some other embodiments, a 12 lead ECG is obtained by using the 3 electrode unit described above coupled with a strap which preferably has at least one or more electrodes, and more preferably up to six electrodes installed thereon (which correspond to the conventional V1 to V6 locations). With the strap featuring at least one or more electrodes, the device is able to derive a 12 lead ECG recording for analysis.

The recording process of the three electrode unit with the strap is similar to that implemented by the three electrode unit without the strap as described above. The electro-cardiac signals from the electrodes located in the strap are preferably recorded simultaneously or at least substantially simultaneously. Communication between the three electrode unit and the strap may optionally be performed with wires for example.

Alternatively the three electrode unit is optionally and preferably used to record electro-cardiac signals from both hands and the lower torso or leg (i.e. the limb leads). After signal acquisition from the limb leads is completed, the unit is then preferably connected to the strap and only then measurements from the V1 to V6 leads (i.e. the precordial leads) are preferably recorded. For this illustrative method, the limb leads and the precordial leads are preferably monitored separately.

According to other embodiments, the device of the present invention optionally and preferably features a plurality of electrodes: two electrodes in contact with an arm and lower torso (preferably in one unit), and at least one electrode on a strap, as well as one electrode on a second unit. The second unit is preferably in contact with the at least one electrode on the strap; if there is a plurality of electrodes on the strap, then the second unit is preferably in contact with the plurality of electrodes on the strap sequentially.

According to still other embodiments, the device of the present invention optionally and preferably achieves a 12 lead ECG by using a unit incorporated with a strap with a first unit having only two electrodes on it (each electrode preferably being located on a different face of the first unit), and a second separate unit containing 2 electrodes, each on a different face of the unit. The recording process of the second unit is preferably similar to that implemented by the 2 electrode unit described above. The recording process of the unit attached to (or connected with) the strap is preferably performed by holding the unit in the free hand (the one not holding the second unit) and moving the unit across the strap so as to record V1 to V6 locations (or alternatively any other suitable upper torso locations).

According to still other embodiments, the device of the present invention optionally and preferably achieves a 12 lead ECG by using a strap with a second unit for obtaining electrode recording from the upper torso. The strap has optionally at least one electrode, but preferably has six electrodes (or any number of electrodes in between). The second unit preferably contacts the electrode(s) on the strap; if there is a plurality of electrodes, then the second unit optionally contacts each electrode separately or alternatively contacts a single location on the strap to which all the electrodes (optionally via wires) are assembled.

According to yet other embodiments, the device of the present invention optionally and preferably achieves a 12 lead ECG by using the 3 electrode unit described above coupled with an external electrode. The external electrode is most preferably implemented as an electrode which may optionally be either disposable or reusable. This exemplary device configuration produces a 4 electrode device able to derive a 12 lead ECG recording for analysis.

The recording process of this embodiment of the device is similar to that implemented by the three electrode unit described previously. For example the ECG recordings may optionally be undertaken by first placing the external electrode on the lower torso or leg, as depicted in FIG. 1A or 1B. The electrode is preferably left to record for the duration of the sampling of the upper torso. Optionally, the three electrode unit is also first placed on the lower torso for an initial recording.

The three electrode unit is now optionally and preferably used to sample recording locations V1 to V6 found on the upper torso (and/or any other suitable chest locations). The device is preferably held to the upper torso with both hands so that locations RA and LA are in contact with the two electrodes on the first face of the device. Similarly, the third electrode on the second face of the device is preferably in contact with locations V1 to V6 each in turn.

Optionally and preferably, the device may record the electro-cardiac signals continuously while the unit is being moved over the upper torso or optionally and alternatively only when the unit is placed on the accurate V1 to V6 locations (or any other suitable chest locations).

According to other embodiments of the present invention, the device may optionally include a port for one or more electrodes (for example 10 electrodes preferably through an analog switch) thus providing monitoring of 12 leads ECG.

According to another embodiment of the present invention, the device may take a form of a glove so that in the 4 electrode embodiment comprising 2 units, in which one electrode is located on the inner surface of the glove thus in contact with the hand wearing it, and the other electrode is located on the external surface of the glove so as to be in contact with the lower torso or leg. A second glove features 2 electrodes, of which one electrode is located on the inner surface of the glove thus in contact with the hand wearing it, and the other electrode is located on the outer surface of the glove so as to be in contact with the upper torso preferably sampling V1 to V6 locations as described previously.

In yet another embodiment, the glove monitoring the upper torso comprises more than one electrode on its external surface so calculating simultaneously 12 lead ECG.

According to other embodiments, the glove features 3 electrodes, one in the inner surface so as to be in contact with the hand wearing the glove, and 2 electrodes in the outer surface, optionally and preferably one in contact with the other hand while the other electrode is in contact, first with the lower torso or leg for recording the limb leads, and then in contact with the upper torso for recording the precordial leads.

The gloves may contain the previously described components, optionally including a screen on an external surface and also preferably including the navigation system described herein. The glove may also take a form of a thimble. The glove may optionally be disposable. One or more other arrangements or implementations as described herein may also optionally and preferably be used for the gloves.

The device or its units can be standalone or be cooperated in other devices including but not limited to belt, clothes, and so on, According to some embodiments of the present invention, after the cardio-electric signals have been acquired (optionally and preferably by using one of the embodiments depicted above), the data is preferably transmitted to a computational device, located in one of the units, which collects the recordings to infer the 12 lead ECG. Such data transfer may also optionally occur during recording. The device preferably uses the computational device in order to decipher the recordings to obtain a known electrocardiograph. The computational device may optionally comprise any type of processor configuration as is known in the art, including without limitation a data processor with memory, a logic gate, firmware, hardware and the like, or any combination thereof. However, processing may optionally be undertaken by an external processor, for example including but not limited to a mobile or cellular telephone, a call center, PDA, laptop computer, desktop computer, or a server, or any other computer as is known in the art.

Optionally and preferably the raw data is communicated to the processor through wireless communications as is known in the art, including but not limited to Bluetooth, cellular protocol, IrDA protocol, optical communication, WiFi, WLAN and the like. Alternatively or additionally, the data may be transmitted to a call center or back office (as described below).

According to some embodiments of the present invention, more accurate acquisition of the cardio-electric signals is optionally and preferably performed with a guidance system. Indeed, it is known in the art that one of the obstacles in obtaining an accurate ECG (particularly when performed by a layperson) is the difficulty of correct placement of the electrode on the V1 to V6 chest locations (or indeed any other suitable upper torso locations).

The guidance or navigation system of the present invention guides the layperson through the correct placements of the above V1 to V6 locations (or any other suitable locations on the body, preferably chest locations). This is optionally and preferably performed by equipping the unit monitoring the upper torso with a component capable of identifying and quantifying different parameters relating to the unit's movement on the upper torso (e.g. distance, speed, acceleration and direction of the movement). This component may use (but is not limited to) a state of the art technology such as the one used to navigate a computer mouse on a computer screen and/or acceleration parameters enabling position determination. For such an optional implementation, such navigation features constant or near-constant contact between the component responsible for movement detection and the skin. Should contact be lost, then preferably the device issues a warning that the localization of the next recordings may be incorrect. A warning also optionally and preferably appears when the recording time is insufficient (so that the signal is not fully acquired) and/or when the signal quality is low.

Alternatively, the second unit's location and movement can be determined using an external camera (for example a cellular telephone camera) recording the upper torso. The parameters of the mobile unit's location in relation to the required V position (location on the upper torso) may optionally be analyzed with one or more image processing algorithms as are known in the art. Optionally, the V location can be determined using ultrasound (either as part of the unit or standalone). The above mentioned parameters may optionally be displayed graphically and/or numerically and/or verbally on a display device or platform.

The navigation system preferably supports interactive positioning of the electrodes. Thus, the displaying device preferably shows the user in real time where the unit that is monitoring the upper torso is located. The software guides the user, preferably from a set, easy to recognize starting point, optionally including but not limited to the right nipple, shoulder, clavicle or any anatomic position that is easily identifiable.

Preferably, the navigation system may be stored and run on an internal platform located in the device itself. Alternatively, the software may optionally be stored and run on various external platforms including, but not limited to, a television, mobile or cellular telephone, laptop computer, PDA any type of computer or the like.

The display device or platform may be, but are not limited to, any suitable conventional display screen (such as the screen of a handheld device (such as cellular phone, PDA, a television, music and/or video player [such as an MP3 player for example] or any other computer screen etc.), and/or "unconventional" devices to be used as a display screen, a designated screen which may be a part of the device or alternatively which may be external to the device, and so on.

In the case of a graphic presentation, the image displayed may be an image of any human body or torso, such as a stylized image for example. Alternatively, the image may be that of the specific user so as to facilitate identification of the required locations. In any of these options the correct V1 to V6 locations are preferably shown on the image, more preferably with the current position of the unit monitoring the upper torso as achieved with the assistance of the guidance system (for example as provided through obtaining an image of the unit on the body, for example optionally with a camera, through ultrasound, or alternatively with some other type of location signaling). In this manner the user is able to know where the unit is currently located in relation to the next correct and appropriate location. Once the appropriate location is reached the system preferably indicates this to the user, for example with a signal such as a light, sound or vibration, or combination thereof, and indicates that a signal is being acquired. Once the signal has been acquired the software may optionally instruct the user to continue on to the next location.

The above navigation system may optionally be implemented in any of the embodiments of the device of the present invention as described herein.

Optionally and preferably, one or more of a plurality of methods may be used in order to ensure correct location of the V1 to V6 locations (which are used herein to indicate any type of recording position on the chest or upper torso). Two optional exemplary methods are an arithmetic mapping method and an anatomical method. The arithmetic method is based on the fact that V1 to V6 points bear a constant proportional distance between each other with regard to the torso dimensions. In this method, before the device is used for the first time the user preferably measures (for example, by using a measurement tape) the distance between two fixed anatomical points on the upper torso, such as the nipples or clavicles, and/or may measure the circumference of the upper torso. The measured distance is then preferably entered to the device by the user (whether directly or through an external device) and a designated algorithm and/or software preferably uses this data to further calculate where the V1 to V6 locations are to be located. Alternatively, the user may optionally move the device itself from the first fixed anatomical point to the second fixed anatomical point so that an automatic measurement of the distance between the two points is performed. After measurement is complete, the device again uses this data in order to calculate where the V1 to V6 locations are located. The calculation of the V1 to V6 locations is then preferably used by the navigation system as described below.

An anatomical method according to the present invention preferably maps the recording points according to one or more anatomical landmarks. The anatomical method has a number of optional implementations. In a first implementation, a trained person preferably sets V1 to V6 points in the device's memory for each specific user according to the chest anatomy, preferably by starting from a reference point by moving the navigation unit. Upon reaching the first point needed to be monitored (V1) the trained person preferably stores its location in the device's memory (more preferably including distance and angle) in relation to the starting point. The process is preferably repeated for the V2 to V6 locations. The next time the user uses the device, the V1 to V6 locations are already stored in the device's memory, so when starting from the same reference point, the device's navigation system will enable the user to reach the required V location. Optionally the person is not trained but is still able to execute the above method.

In another implementation an image of a human torso is preferably provided with the device, on which the correct V1 to V6 locations are marked. The user holds the image in front of the body and preferably uses it as a reference to locate the V1 to V6 locations on the body.

In yet another implementation of this method a photograph of the torso is obtained and sent to a call center or back office (described below) through any known mechanism, including but not limited to MMS, e-mail or any other transmission method. Trained personnel in the center or office preferably mark the V1 to V6 locations on the picture and return it to the user for a reference as described herein. Such markings may also optionally (additionally or alternatively) be added automatically by the software on the image. This may also optionally be performed interactively for example through the transmission of video over the Internet or other network for guiding the user in real time to mark the correct V1 to V6 locations.

In the arithmetic and anatomical methods, the V1 to V6 locations are preferably stored in the device's memory. The next time the user uses the device, the V1 to V6 locations are preferably already stored in the device's memory, so that by using the device's navigation system, the user is able to locate the V1 to V6 locations.

Optionally the localization of the recording location may be accomplished with an external strap or belt that predefines the recording locations. The optional external strap or belt may optionally function as an accessory to the device and is preferably worn by the user around or over the upper torso with the V1 to V6 recording locations predetermined, wherein each of the recording location preferably has a recess and/or hole and/or indentation and/or some sort of a mark and/or some type of protrusion that enables the correct placement of the unit monitoring the upper torso on the accurate locations of V1 to V6.

The strap, belt or any other similar device for correct placement of the unit monitoring the upper torso, may optionally be disposable and is optionally and preferably integrated into the device in such a way that it is extendible from the device and optionally held in place on location, optionally using material including but not limited to a clamp, clip, removable adhesive tape, or the like.

According to some embodiments of the present invention, the structure and configuration of the device may optionally be constructed in a plurality of different implementations. Preferably, the basic device (or unit) comprises an A/D converter, processor, communication module, I/O module, filter module, memory, power source, amplifier, and electrodes. The power source may optionally be a battery, which may optionally be used once or which may be rechargeable. Optionally the device may be fitted with a display device including but not limited to an LCD screen, plasma screen, LED array or the like. The input output module may optionally be implemented using a wired or I/O port for example including a plurality of but not limited to USB port, serial port, optical port, PCMCIA, Ethernet, IDA, cellular telephone jack or port, or the like. The communication module for example may include but is not limited to Bluetooth, WiFi, IrDA, WLAN, modem, dual communication, or the like. Optionally the I/O or communication modules of the present invention may be used to communicate in real time the recorded ECG signal to an external display unit including but not limited to a PDA, computer screen, television screen, mobile phone display or monitor, or the like (or a combination thereof). The electrode configuration of the device may optionally be configured in a number of ways exemplary described below in various embodiments.

The device of the present invention preferably comprises memory. The memory may optionally store medical information, and is preferably used to store medical history, most preferably including information regarding the cardiac history and status of the user (including but not limited to catheterization results, prior ECG's, echo results, stress test results and the like). The data can optionally be stored as video (for example for an angiogram, echocardiogram etc), images (for example CT, MRI), audio information and so on. Comparing the current ECG recording to the previously obtained ECG, which is stored in the device's memory, may increase specificity and sensitivity of diagnosis of cardiac abnormalities. Additionally the user's medical history may optionally and preferably be accessed in case of an emergency by medical personnel and may also be used for identifying the specific user. Optionally this memory also stores the upper torso locations as described above.

According to some embodiments of the present invention, there is provided a mechanism to correctly identify the subject on whom the ECG was measured, as well as (additionally or alternatively) to preserve the privacy of such a subject. Due to the sensitive and personal information that may be contained in the memory of the device a number of optional identification confirmation measures may optionally be used to ensure that the device and the data contained within it, is personally accessed by the subject (and/or is accessed by authorized personnel such as medical personnel) using one or more authentication and identification methods. Such methods may optionally include but are not limited to, username and password, biometric identification (including but not limited to fingerprint or retinal scan), RFID and the like. Optionally the device of the present invention may utilize a hash function to encrypt the subject's sensitive data or used for the identification of the subject.

According to some embodiments of the present invention, there are provided methods to interpret the ECG data. For example, optionally the electro-cardiac data is analyzed by the device's internal computational platform. The results are then optionally and preferably translated into an audio (preferably at least partially verbal) and/or graphic presentation which may be manifested on the display unit (for example the device may relay to the layperson whether there is a need for medical assistance and its urgency; and/or indicate to trained personnel the exact condition the user is suffering from).

Optionally, in case of an emergency the device may automatically contact the emergency services (for example, if the device is connected to a cellular telephone, an emergency call may optionally be placed through the telephone and/or any other type of telephone number).

According to another optional embodiment, which may optionally be implemented alternatively or additionally to the above embodiment, the cardio-electric signals are preferably transmitted to a back office or call center service. Trained personnel and/or designated software located therein preferably analyze and decipher the signals. Alternatively, the transmitted data may optionally contain the already processed ECG recording, such that the trained personnel and/or designated software need only to analyze the information (and relay it to the user). The processed or preprocessed raw data is optionally and preferably communicated to back office or the call center through any suitable communication mechanism as described herein.

The results may optionally be transmitted back to the user through any suitable communication mechanism as described herein, optionally including but not limited to MMS, SMS, two way communication module, voice communication, mobile or landline telephone, email, facsimile, a printer, or the like. Alternatively, trained personnel may optionally contact the user and provide medical advice according to the results (as well as optionally contacting local emergency services if required). Alternatively, the user is preferably able to contact the back office or call center in order to convey further information regarding the user's condition and/or receive the results for the signals previously sent by the device.

Optionally the medical information stored in the device may also be sent to the back office or call center. A professional consultation may optionally be provided in real time based on medical information, real time ECG and user's communicated medical information regarding current and/or prior symptoms or illnesses. This enables implementation of an exemplary 'pay per call' model, such that the user pays for each such consultation separately (at the time of consultation).

Optionally, in case of an emergency the user may be located utilizing an optional GPS component installed in the device so that the user's exact location may be ascertained. Alternatively, the user's location may optionally be identified using an external locating component (such as the one existing in the cellular connected to the device).

According to some embodiments, one or more other optional features may optionally be provided. Optionally, the device may be accompanied with an adaptor which will enable communication between the device and any sort of handheld devices (e.g. cellular phones, PDAs etc.). The adaptor may be specifically tailored to the model of the handheld device used. An adaptor may also optionally be provided with regard to a power source and so forth.

The device of the present invention may provide the option of performing many additional cardiac diagnostic tests some of which may require continuous use, for example including but not limited to performing a continuous type of monitoring known as a Holter test, or a stress test. Without wishing to be limited in any way, it should be noted that the test as described herein with the present invention may optionally be performed in a setting that is convenient and comfortable to the user, eliminating or at least reducing the need to perform these tests in a hospital setting. Such a test could optionally be performed as a "self" stress test which the user performs according to one or more instructions from the software.

Optionally the device may include communication with one or more other accessories (whether external or internal), such as a Pulse Oximeter, stethoscope, ultrasound transducer, echocardiogram transducer, thermometer, capnograph, blood pressure cuff, fetal heart rate transducer, camera, defibrillator electrodes, wire electrodes, inhaler, cardiac enzyme detector, blood sugar level analyzer and so forth. These accessories may, alternatively, be connected to the device optionally through one of the I/O plugs or wirelessly. The additional accessories may improve the diagnostic ability of the device and provide a well rounded depiction of the user's state of health.

The above mentioned ultrasound transducer may utilize the device's navigation system in order to reach the conventional ultrasound locations. The ultrasound may monitor different heart functions (such as the motion of the walls, the valve functions etc.). The device is preferably able to compare between the stored ultrasound parameters and the acquired real time parameters which for increasing the sensitivity of detection of heart abnormalities. A stethoscope may optionally be used in a similar manner for locating the monitoring points using the navigation system.

The device of the present invention may optionally be further utilized as a personal defibrillator. The power supply required in order to activate the defibrillator option may optionally be either internal (i.e. within the device itself) or external. The defibrillation feature may be optionally be activated by a remote source (such as the medical personnel in the call center or back office); by the user himself; or by a bystander (preferably after receiving authorization from the device itself or from the call center or back office).

Such remote activation may optionally be performed for example through cellular telephone communication or any other type of remote communication, such that activation is preferably performed in a secure manner. The defibrillator may optionally use the electrodes of the device itself and/or additional electrodes, preferably attached to a belt such that each electrode is in contact with a different portion of the torso of the user. Optionally, the user who is suspected of having a heart attack or any other situation which may lead to lethal arrhythmia (and/or any other medical situation requiring defibrillation) may connect the electrodes (or optionally the device's units) onto the upper torso, preferably assuring attachment to the skin by using a belt or strap, such that defibrillation (optionally activated automatically or semi-automatically as specified above) is enabled even if the user's level of consciousness is reduced.

Furthermore, the device of the present invention may optionally be coupled with a recess for carrying a medicament that is stored for emergency purposes. For example including but not limited to aspirin or a blood thinner or other beneficial medicament that may be safely taken to reduce the effect of a cardiac ischemia. Optionally, the medicament may be a prescription drug specific to the user to take in case of emergencies.

According to some optional embodiments, each electrode may optionally feature a gel dispenser for dispensing conductive gel, for example upon contact with the skin and/or upon application of pressure and/or by pressing a designated button releasing the gel.

It should be noted that throughout, the term "user" is optionally used to indicate the subject on which the measurements are being performed, such that the user performs the measurements on him/herself; however, it is possible that the user is different from the subject, in which case the method(s) as performed may optionally differ as required and/or suitable.

Unless otherwise indicated, the term "recording" in reference to one or more electrodes may optionally refer to a signal which is detected in real time but which is not necessarily stored.

The term "lower torso" preferably refers to the left leg and lower left torso.

Preferably recording at the limb leads is performed simultaneously.

Preferably, although it is described herein for some embodiments that a plurality of electrodes are on the same face of a subunit and/or of the device, these electrodes are preferably separated by a distance, and may also optionally and preferably be located on different faces of the device and/or subunit.

Optionally and preferably, at an initial stage of recording measurements, a calibration is performed, optionally with the reference point and/or before recording a first measurement. The calibration preferably includes sending a test signal, for example of about 1 millivolt, determination of the level of resistance between the electrode and the skin and also optionally quantification of the level of noise associated with recording, for example from the muscle.

According to an optional embodiment, of the present invention provides for a device for performing a 12 lead ECG on a body of a subject, comprising only three electrodes, wherein at least one electrode records a plurality of measurements at a plurality of different locations on the body of the subject.

Optionally and preferably each electrode is in contact with a different part of the body of the subject.

Optionally and preferably a plurality of electrodes is in contact with a lower torso or leg of the body of the subject, while at least one electrode is in contact with a plurality of different locations on an upper torso of the body of the subject.

Optionally and preferably a plurality of different locations is located on the subject's body.

Optionally and preferably the plurality of different locations correspond to V1 to V6.

Optionally and preferably at least one electrode is sequentially in contact with said plurality of different locations.

Optionally and preferably the plurality of electrodes is in contact with a surface of the body of the subject simultaneously or substantially simultaneously with said at least one electrode being in sequential contact with said plurality of different locations.

Optionally and preferably the device according to the present invention further comprising a housing, wherein one electrode is located on a lower surface of said housing and wherein a plurality of electrodes are located on an upper surface of said housing.

Optionally and preferably the housing comprises two units, a first unit comprising an electrode on a lower surface of said housing and an electrode on an upper surface of the housing, and a second unit comprising an electrode on the upper surface of the housing.

Optionally and preferably the units are connected with a wire.

Optionally and preferably at least one electrode is connected to the housing with a wire.

According to an optional embodiment, of the present invention provides for a device for performing a 12 lead ECG on a body of a subject, comprising an electrode array, the electrode array including only three electrodes for recording a measurement, wherein at least one electrode records a plurality of measurements at a plurality of different locations on the body of the subject.

According to an optional embodiment, of the present invention provides for a device for performing a 12 lead ECG on a body of a subject, comprising an electrode array, the electrode array consisting of three electrodes for recording a measurement, wherein at least one electrode records a plurality of measurements at a plurality of different locations on the body of the subject.

According to an optional embodiment, of the present invention provides for a device for performing a 12 lead ECG on a body of a subject, comprising only four electrodes for recording a measurement, wherein at least one electrode records a plurality of measurements at a plurality of different locations on the body of the subject.

Optionally and preferably each electrode is in contact with a different part of the body of the subject.

Optionally and preferably a plurality of electrodes is in contact with a lower torso or leg of the body of the subject, while at least one electrode is in contact with a plurality of different locations on an upper torso of the body of the subject.

Optionally and preferably, a plurality of different locations is located on a chest of the body of the subject.

Optionally and preferably a plurality of different locations correspond to V1 to V6.

Optionally and preferably at least one electrode is sequentially in contact with said plurality of different locations.

Optionally and preferably a plurality of electrodes is in contact with a plurality of locations on the lower torso or leg of the body of the subject simultaneously or substantially simultaneously with at least one electrode being in sequential contact with said plurality of different locations.

Optionally and preferably the device according to the present invention further comprises a housing, the housing comprises two units, each unit comprising an electrode on a lower surface of the housing and an electrode on an upper surface of the housing.

Optionally and preferably the housing comprises two units, one unit comprising two electrodes on the lower surface of said housing and an electrode on the upper surface of said housing and a second unit comprising one electrode.

Optionally and preferably at least one electrode is connected to said housing with a wire.

According to an optional embodiment, the present invention provides for a device for performing a 12 lead ECG on a body of a subject, comprising an electrode array, the electrode array including only four electrodes for recording a measurement, wherein at least one electrode records a plurality of measurements at a plurality of different locations on the body of the subject.

According to an optional embodiment, the present invention provides for a device for performing a 12 lead ECG on a body of a subject, comprising an electrode array, the electrode array consisting of four electrodes for recording a measurement, wherein at least one electrode records a plurality of measurements at a plurality of different locations on the body of the subject.

According to an optional embodiment, the present invention provides for a system for performing a 12 lead ECG on a body of a subject, comprising: a processor for executing at least one instruction for processing the measurements.

Optionally and preferably the device according to the present invention further comprises a housing for the processor and the device.

Optionally and preferably the processor is separate from the device.

Optionally and preferably the processor is comprised in a computer selected from the group consisting of a cellular telephone, a laptop computer, a smartphone, a PDA and a pager.

Optionally and preferably according to the present invention the present invention further comprises accounts for a remote location for analyzing said measurements.

Optionally and preferably the location features medical personnel.

Optionally and preferably the device of the present invention further comprising a dynamic reference electrode between a plurality of electrodes is calculated in relation to said reference electrode, sequentially or simultaneously.

Optionally and preferably the preferred embodiments according to the present invention each plurality of electrodes functions as a dynamic reference electrode in turn for each limb lead calculation.

Optionally and preferably the preferred embodiments according to the present invention further comprises a calculator for determining an arithmetic calculated value as a reference.

Optionally and preferably the preferred embodiments according to the present invention further comprising signal acquisition component for acquiring the signals from the electrodes.

Optionally and preferably the preferred embodiments according to the present invention further comprising a signal amplification component.

Optionally and preferably the preferred embodiments according to the present invention further comprising a noise reduction component.

Optionally and preferably the preferred embodiments according to the present invention further comprising a data transmission component.

Optionally and preferably the preferred embodiments according to the present invention further comprising a memory component.

Optionally and preferably the memory component stores coordinates for at least one recording location on the body.

Optionally and preferably the coordinates relate to V1 to V6 locations.

Optionally and preferably the memory component further stores an image of the body of the subject and said coordinates are marked on said image.

Optionally and preferably the memory stores medical information of the subject.

According to an optional embodiment, the present invention provides for a navigation system for locating the plurality of different recording locations.

Optionally and preferably the navigation system includes a visual display.

Optionally and preferably the navigation system includes an audio display.

Optionally and preferably the navigation system includes a vibrating component.

Optionally and preferably the visual display, audio display or vibrating component alerts a user as to at least one recording location.

Optionally and preferably the navigation system is incorporated within the device according to an optional embodiment of the present invention.

Optionally and preferably the navigation system is incorporated in a separate external device.

Optionally and preferably the separate external device comprises a computer selected from the group consisting of a cellular telephone, a laptop computer, a smartphone, a PDA and a pager.

Optionally and preferably the device according to the present invention further comprising a strap for determining said plurality of different locations.

Optionally and preferably the device according to the present invention further comprises a defibrillator.

Optionally and preferably the device according to the present invention further comprises at least one accessory selected from the group consisting of a Pulse Oximeter, stethoscope, ultrasound transducer, echocardiogram transducer, thermometer, capnograph, blood pressure cuff, fetal heart rate transducer, camera, defibrillator electrodes, wire electrodes, a carrier for a medicament and a combination thereof.

According to some optional embodiment, the present invention provides for a method for obtaining a 12 lead ECG reading from three or four electrodes on a body of a subject, comprising:

a) obtaining at least one measurement from a location selected from the group consisting of a limb or the lower torso; and b) obtaining a plurality of upper torso measurements.

Optionally and preferably obtaining at least one measurement from a location selected from the group consisting of a limb or the lower torso comprises obtaining at least one measurement from an arm.

Optionally and preferably the arm comprises a hand.

Optionally and preferably at least one measurement is obtained from a wrist.

Optionally and preferably a plurality of measurements is obtained from both arms.

Optionally and preferably the plurality of upper torso measurements comprises measurements at V1 to V6.

Optionally and preferably prior to obtaining the plurality of measurements, a plurality of recording locations is determined on the body of the subject.

Optionally and preferably the plurality of recording location is determined by measuring the body of the subject.

Optionally and preferably the plurality of recording locations is determined from an image of the body of the subject.

Optionally and preferably the plurality of recording locations is automatically determined from said image of the body of the subject by software.

Optionally and preferably the plurality of recording locations is determined from said image of the body of the subject by manually marking said locations on said image.

Optionally and preferably the method according to an optional embodiment of the present invention further comprises transmitting said measurements to a remote location.

Optionally and preferably the method according to an optional embodiment of the present invention further comprises defibrillating the subject according to said measurements.

Optionally and preferably the defibrillating is activated by a remote location.

Unless otherwise defined, all technical and scientific terms used herein have the same meaning as commonly understood by one of ordinary skill in the art to which this invention belongs. The materials, methods, and examples provided herein are illustrative only and not intended to be limiting. Implementation of the method and system of the present invention involves performing or completing certain selected tasks or stages manually, automatically, or a combination thereof. Moreover, according to actual instrumentation and equipment of preferred embodiments of the method and system of the present invention, several selected stages could be implemented by hardware or by software on any operating system of any firmware or a combination thereof. For example, as hardware, selected stages of the invention could be implemented as a chip or a circuit. As software, selected stages of the invention could be implemented as a plurality of software instructions being executed by a computer using any suitable operating system. In any case, selected stages of the method and system of the invention could be described as being performed by a data processor, such as a computing platform for executing a plurality of instructions.

Although the present invention is described with regard to a "computer" on a "computer network", it should be noted that optionally any device featuring a data processor and/or the ability to execute one or more instructions may be described as a computer, including but not limited to a PC (personal computer), a server, a minicomputer, a cellular telephone, a smart phone, a music player, a game console, a PDA (personal data assistant), a pager, an ATM machine or a cashpoint. Any two or more of such devices in communication with each other, and/or any computer in communication with any other computer may optionally comprise a "computer network".

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 2A-I are exemplary depiction of the electrode configuration according to some preferred embodiments of the present invention;

FIGS. 4A and 4B are exemplary block diagram of an electrode navigation system according to the present invention;

DESCRIPTION OF THE PREFERRED EMBODIMENTS

Figure 1B:
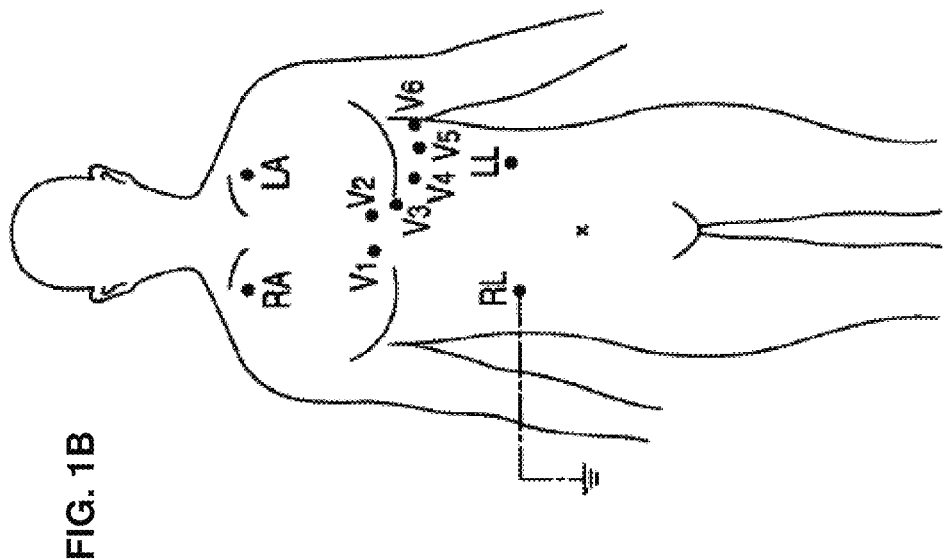
FIG. 1A-B diagrammatically depict the conventional electrode locations to obtain a 12 lead ECG recording.

The present invention is of a system, personal device and a method for recording a 12 lead ECG and/or other biological signals by using a small number of electrodes. According to some embodiments, three electrodes are used while according to other embodiments, four electrodes are used. Each electrode is preferably in contact with a different body part. Optionally, the electrodes are contained in one unit but preferably the electrodes are divided between two units. More preferably, the two units communicate with each other, optionally through wires for example.

The electrodes may optionally be distributed between the units (if more than one is present) according to any suitable configuration, including the exemplary configurations described herein. Regardless of the exact configuration, according to some embodiments, a method for obtaining a 12 lead ECG reading from three or four electrodes preferably includes obtaining at least one measurement from a location selected from the group consisting of a limb or the lower torso, and a plurality of upper torso measurements.

According to some embodiments, a dynamic reference electrode is used for ECG recording such that each electrical difference between two or more electrodes is calculated in relation to one or more other (reference) electrode(s) sequentially or simultaneously (although preferably simultaneously or at least in parallel). The reference electrode (s) is an electrode that is not involved in direct measurement of electrical dipole. For each lead calculation the reference electrode is different (hence 'dynamic'), so in a system comprising only 3 electrodes, the reference electrode is different and shifts for each lead measurement. This may be done by a designated software and/or hardware optionally comprising a switch. This is preferably done in order to calculate the limb leads.

Alternatively or additionally, an arithmetically calculated value may optionally be used as a reference, for example as described herein.

Preferably, each unit may also contain a signal acquisition component for acquiring the signals from the electrodes. Optionally and preferably, one or more units (if more than one is present) may optionally feature a data processing capability. Alternatively, such data processing may optionally be performed remotely. Optionally and more preferably, a component enabling signal amplification and/or a component enabling background noise reduction is provided at one or more units.

According to some embodiments, a device according to the present invention features a component enabling data transmission, preferably through wireless transmission although optionally through wired transmission. The device may optionally be implemented as a "stand-alone" device or alternatively may be implemented as an accessory device to any type of computer and/or device with transmission capabilities as described herein, including but not limited to a cellular telephone, PDA, laptop or other computer and the like.

According to other embodiments, a navigation or guidance system is preferably provided for enabling the user to locate the correct locations for obtaining the ECG measurements, more preferably for locating one or more of the points required for monitoring ECG over the upper torso (such as the chest V1-V6 locations for example). More preferably, the system includes some type of automatic notification of at least one correct location for obtaining a measurement, which most preferably includes one or more of a visual display, audible sound, flashing light or any other type of alert.

The location is optionally and preferably calculated according to the relations of fixed reference surface anatomical landmarks, more preferably including at least the mathematical relationship between the location of the clavicles and iliacs to V1-V6 locations on the upper torso. Alternatively or additionally one or more other locations may optionally be so calculated.

Alternatively or additionally, the location(s) for measurements on a particular part of the body may optionally be determined according to a physical device such as a strap, for example with markings, holes and so forth, which is placed on the part of the body (preferably the upper torso). Such a strap may optionally (alternatively or additionally) feature one or more additional electrodes for obtaining an ECG measurement.

As described herein, according to some embodiments one or more additional electrodes may optionally provided for obtaining an ECG measurement at one or more locations.

Also according to some embodiments of the present invention, a defibrillator is provided, optionally in combination with the device for measuring the ECG (but alternatively separate from the device). Operation of the defibrillator is preferably at least partially determined according to a measurement obtained by the device, but may also optionally (additionally or alternatively) be at least partially determined according to one or more medical personnel (whether local or remote, for example in a call center).

Optionally the device may include one or more other accessories, such as a Pulse Oximeter, stethoscope, ultrasound transducer, echocardiogram transducer, thermometer, capnograph, inhaler, cardiac enzyme detector, blood pressure cuff, fetal heart rate transducer, camera, defibrillator electrodes, wire electrodes and so forth. These accessories may, alternatively, be connected to the device optionally through one of the I/O plugs and/or wirelessly. The additional accessories may improve the diagnostic ability of the device and provide a well rounded depiction of the user's state of health.

The principles and operation of the present invention may be better understood with reference to the drawings and the accompanying description.

Referring now to the drawings, FIG. 1 is a schematic diagram of the recording locations utilized to produce a 12 lead ECG measurement according to the background art. Traditionally these recording locations are used with wired recording electrodes to produce the 12 lead ECG. These recording locations are also preferably used by the device of the present invention to determine the 12 lead ECG; however, according to some embodiments a four or three electrode configuration is used, such that fewer electrodes are used than are known in the art. The recording locations are labeled as follows. LL is the left leg (this location may optionally be anywhere on the lower portion of the torso as shown in FIG. 1B). RL is the right leg (again this location may optionally be anywhere on the lower portion of the torso as shown in FIG. 1B). LA is the left arm; the electrode may optionally be placed anywhere along the arm, including the fingers, up to and including the shoulder region as seen in FIG. 1B. RA is the right arm which may also optionally be so placed. The upper torso or chest has six recording locations labeled V1, V2, V3, V4, V5 and V6. These recording points are preferably used in combination in the method of the present invention to infer the 12 lead ECG, although it should be noted that optionally the upper torso or chest locations may be modified as is known in the art.

FIG. 2A is a schematic block diagram of an exemplary, illustrative embodiment of a device 200 according to the present invention which uses a 4 electrode configuration such that a 12 lead ECG is inferred from 4 recording electrodes 202, 204, 206 and 208 respectively. The electrodes 202, 204, 206 and 208 are placed over the recording sites that are used in the standard 12 lead ECG recording as described above. The device optionally and preferably comprises two subunits 201 and 205 respectively. Preferably each subunit 201 and 205 additionally comprises the components described in FIG. 3 below.

Subunit 201 preferably comprises two recording electrodes 202 and 204 located on a different face of the device, such that a first face 203 of subunit 201 comprises one electrode 204, while a second face 207 of subunit 201 comprises the second electrode 202. Similarly the second subunit 205 comprises electrode 206 on first face 211 while electrode 208 is placed on the second face 209. Therefore device 200 comprises a total of 4 electrodes.

The recording electrode 204 on a first face 203 is preferably in contact with a first recording location while the electrode 202 of second face 207 contacts a second, different, recording location. Similarly, electrode 206 of first face 211 of the second unit is in contact with another recording location while the electrode 208 of second face 209 contacts yet another, different, recording location. Therefore together subunit 201 and 205 preferably are in contact with multiple different recording locations.

Figure 1A:
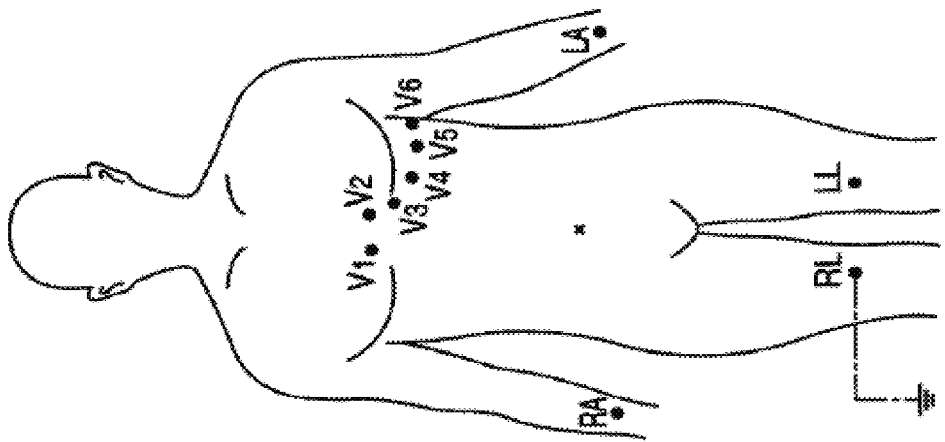

For example an ECG recording may be exemplarily undertaken as follows. Subunit 201 of device 200 is preferably used to simultaneously (or substantially simultaneously) record a different location from subunit 205. For example, subunit 201 may optionally be placed at a location that corresponds to recording location LL (as depicted in FIG. 1A or 1B). The first electrode 204 on first face 203 of subunit 201 is preferably in contact with recording locations LL, while second electrode 202 on face 207 of first subunit 201 preferably is in contact with the hand holding subunit 201 in place over location LL. Therefore the second electrode 202 of first subunit 201 is in contact with recording location LA. Similar, subunit 201 may optionally be used to record at locations RL and RA for example, and/or for any combination of arm and leg locations.

Simultaneously (or at least substantially simultaneously), the second subunit 205 is in contact with recording locations V1 to V6 found on the chest (as depicted in FIG. 1A-B), preferably in a sequential manner between these locations. The second subunit 205 of the device is preferably held to the upper torso or chest with the right hand such that recording location RA is in contact with the first electrode 206 on the first face 211 of second subunit 205 (ie in contact with the hand). Recording locations V1 to V6 are in contact with the second electrode 208 found on the second face 209 of subunit 205 while in contact with the skin surface of the chest or upper torso. Preferably the second face 209 of the second subunit 205 comprising second electrode 208 is held to the chest while the second subunit 205 is moved across the chest. In moving across the chest, each recording location V1, V2, V3, V4, V5, and V6 are preferably sequentially sampled in turn (as seen in FIG. 1A-B). Optionally, recording locations V1 to V6 are located by the user with a guidance system as described below in FIG. 4 that may optionally guide the user to locate the correct recording locations.

Optionally first subunit 201 and second subunit 205 are in contact with one or more wires.

FIG. 2B depicts the configuration of another optional embodiment of a device according to the present invention with 4 electrodes, namely, electrodes 212, 214, 216 and 218 in two subunits 213 and 215. Device 210 is preferably configured as described in FIG. 2A above, except that subunit 215 is preferably different. Optionally the first subunit 213 is preferably implemented as described above, while second subunit 215 may be optionally and preferably be implemented with a single disposable electrode unit 217 having two electrodes 216 and 218, preferably one on each face of electrode unit 217, such that electrode surface 216 is on the lower face while electrode surface 218 is on the upper face.

The method of obtaining a sample using this configuration is implemented similarly to that used in device 200 described in FIG. 2A above.

FIG. 2C depicts the configuration of another optional embodiment of a device according to the present invention with 3 electrodes as shown by device 220. Most preferably the 3 electrodes are configured such that two electrodes 222 and 224 are located on a first face 225 of the device 220 while a second face 227 comprises a third electrode 226 (may optionally be located on the sides of device 220 for example).

The method of obtaining the 12 lead ECG recording is preferably performed as follows. At first, device 220 is preferably held such that each of the three electrodes 222, 224 and 227 is in contact with a different limb. For example, the ECG recordings may be undertaken by first placing device 220 at a location on the lower torso or legs wherein second face 227 (and hence third electrode 226) is in contact with the skin of the lower torso or one of the legs. Device 220 is preferably held by both hands such that contact is made with each of the two electrodes 222 and 224 on first face 225 to each hand, corresponding to the RA and LA locations.

After the recording (and optionally also calculation) is completed, device 220 is preferably used to sample recording locations V1 to V6 found on the chest (and/or any other suitable locations on the upper torso). The device 220 is preferably held to the upper torso with both hands, preferably thereby maintaining contact with the two electrodes 222 and 224 on first face 225 as described above. Similarly, electrode 226 found on the second face 227 of device 220 is preferably used to sequentially sample recording locations V1 to V6 each in turn, optionally and preferably with the guidance of the software described below (FIG. 4). Preferably second face 227 of device 220 comprising the third electrode 226 is held to the chest and/or upper torso while the subunit is gradually moved across the chest and/or upper torso.

FIG. 2D depicts the configuration of another optional embodiment of a device according to the present invention with the 3 electrode configuration of device 220 preferably coupled to an external electrode 238, producing device 230. External electrode 238 is most preferably realized as a disposable electrode however it may optionally be realized as an electrode that includes but is not limited to a disposable electrode or a reusable electrode. The use of the present device 230 configuration produces a 4 electrode device able to derive a 12 lead ECG recording for analysis.

The recording process is similar to that implemented by the three electrode unit 220 described above. For example the ECG recordings may be undertaken by first placing external electrode 238 on the lower torso or leg, (as depicted in FIG. 1A or 1B). The electrode 238 is preferably left to record for the duration of the sampling of the chest and/or upper torso. The three electrode unit 220 is now used to sample recording locations as described above. Optionally, unit 220 is also first placed on the lower torso for an initial recording of the limb leads.

Figure 2E:
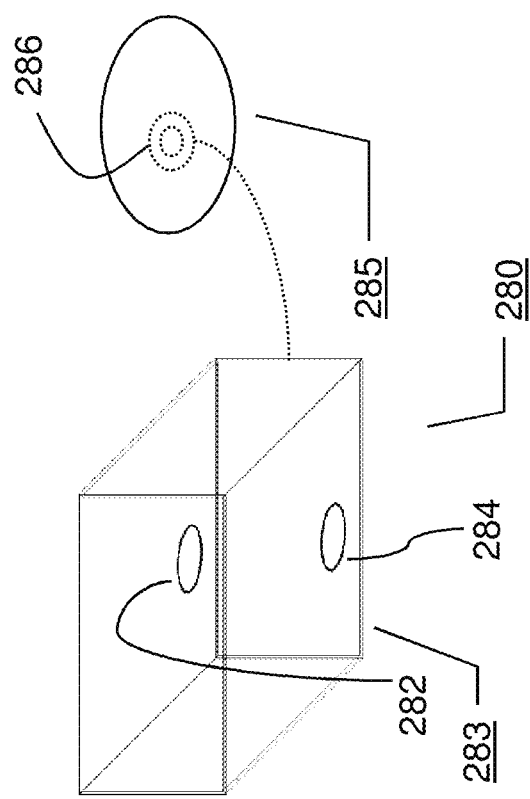

FIG. 2E shows another exemplary, illustrative embodiment of a device 280, which is similar to device 210 of FIG. 2B, except that only one electrode 286 is present on a second subunit 285, while a first subunit 283 features two electrodes 282 and 284. Second subunit 285 may optionally and alternatively be configured as for first subunit 283 with regard to one or more optional additional components as described herein (apart from a second electrode).

FIG. 2F shows another exemplary, illustrative embodiment of a device 240 in the form of a wristwatch, preferably featuring an electrode 242 for contacting the arm on which device 240 is worn. Device 240 also preferably features an electrode 244 on an external surface of strap 245 such that electrode 244 contacts one location on the body of the subject (such as a leg for example), as well as an electrode 246 (shown with an optional wired connection to device 240) for contacting a plurality of locations on the body of the subject (such as the upper torso for example).

FIG. 2G shows another exemplary, illustrative embodiment of a device 250 in the form of a wristwatch, preferably featuring an electrode 252 for contacting the arm on which device 250 is worn. Device 250 also preferably features an electrode 254 on an external surface of a strap 255 such that electrode 254 contacts one location on the body of the subject (such as a leg for example), as well as an electrode 256 (shown with an optional wired connection to device 240) for contacting a plurality of locations on the body of the subject (such as the upper torso for example) with an electrode 258 for contacting another arm, such as a hand for example.

FIG. 2H is similar to FIG. 2G, except that in place of an optional wired connection, electrodes 268 and 266 are preferably contained in a second subunit 263.

FIG. 2I features an illustrative device 270, with an electrode 278 on an inner surface of a strap 276 preferably contacting the skin of the wrist (not shown), while another electrode 272 contacts another part of the body such as a part of the other arm for example, and electrode 274 on an external surface of strap 276 preferably contacts a plurality of locations on the body of the subject (such as the upper torso for example).

Figure 3:
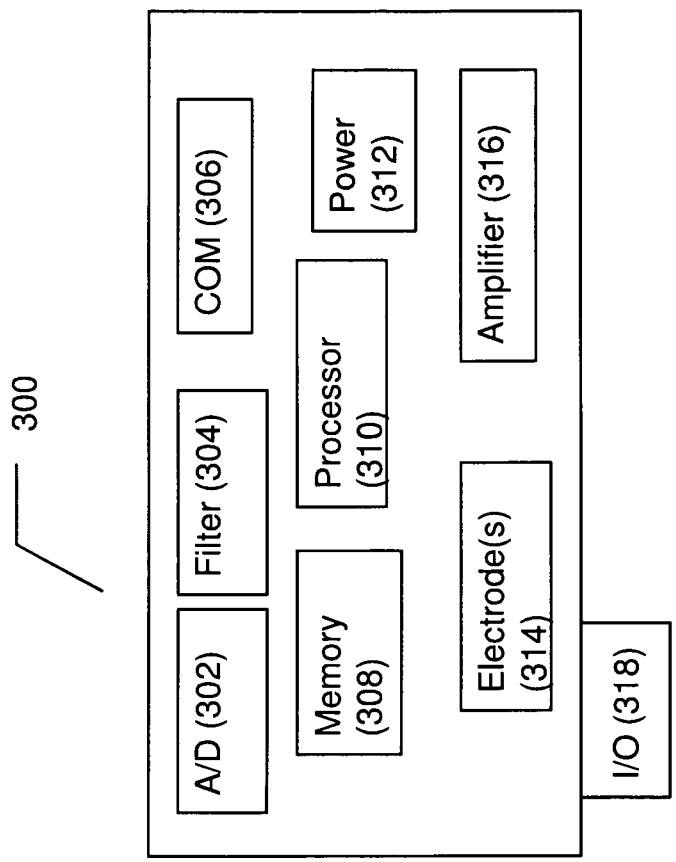
FIG. 3 is an exemplary embodiment of the device of the present invention.

FIG. 3 depicts an exemplary embodiment of a device 300 according to the present invention, preferably featuring an A/D converter 302 (for analog to digital conversion of a signal). Device 300 preferably features a processor 310 for at least performing the calculations as described herein. Device 300 also preferably features a communication module 306, an I/O module 318, a filter module 304, a memory 308, an amplifier 316, and a plurality of electrodes 312.

Optionally the device 300 may be fitted with a display (not shown), including but not limited to an LCD screen, plasma screen, LED array or the like. I/O module 318 may optionally be implemented using a wired or wireless communication port for example including but not limited to USB port, serial port, optical port, PCMCIA, Ethernet, IDA or the like. The communication module 306 for example may include but is not limited to Bluetooth, WiFi, IrDA, WLAN, modem, two way communication, or the like. Communication module 306 may optionally be used to communicate between subunits of the device (not shown) or with a mobile phone (not shown), PDA (not shown) or a call center (not shown). Communication module 306 can optionally provide communications between the device's subunits and/or between the device and external device, or alternatively two separate communication modules 306 can be used (not shown). Communication module 306 and I/O module 318 may be utilized to transfer processed or preprocessed recording. Optionally the I/O module 318 and communication module 306 of the present invention may be used to communicate with an external display unit including but not limited to a PDA, computer screen, TV screen, mobile phone display or monitor.

A recording with the device occurs by use of electrodes 314 as described herein. The electrodes 314 sense the changing dipole at the skin surface where each electrode 314 is in direct contact, then the analog to digital converter 302 preferably converts the analog data to digital data which is then more preferably amplified 316 and filtered 304 according to state of the art known algorithms, producing the raw data. Preferably, the raw data is then processed by processor 310 (for example for at least performing the calculations as described herein) and optionally stored in memory 308 or transmitted using communication module 306 or I/O module 318. Optionally the raw data is communicated using I/O 318 or communication module 306 to an external processor (not shown). The external processor may be realized in various forms including but not limited to a PDA, computer, call center, mobile phone, or the like.

Figure 4B:
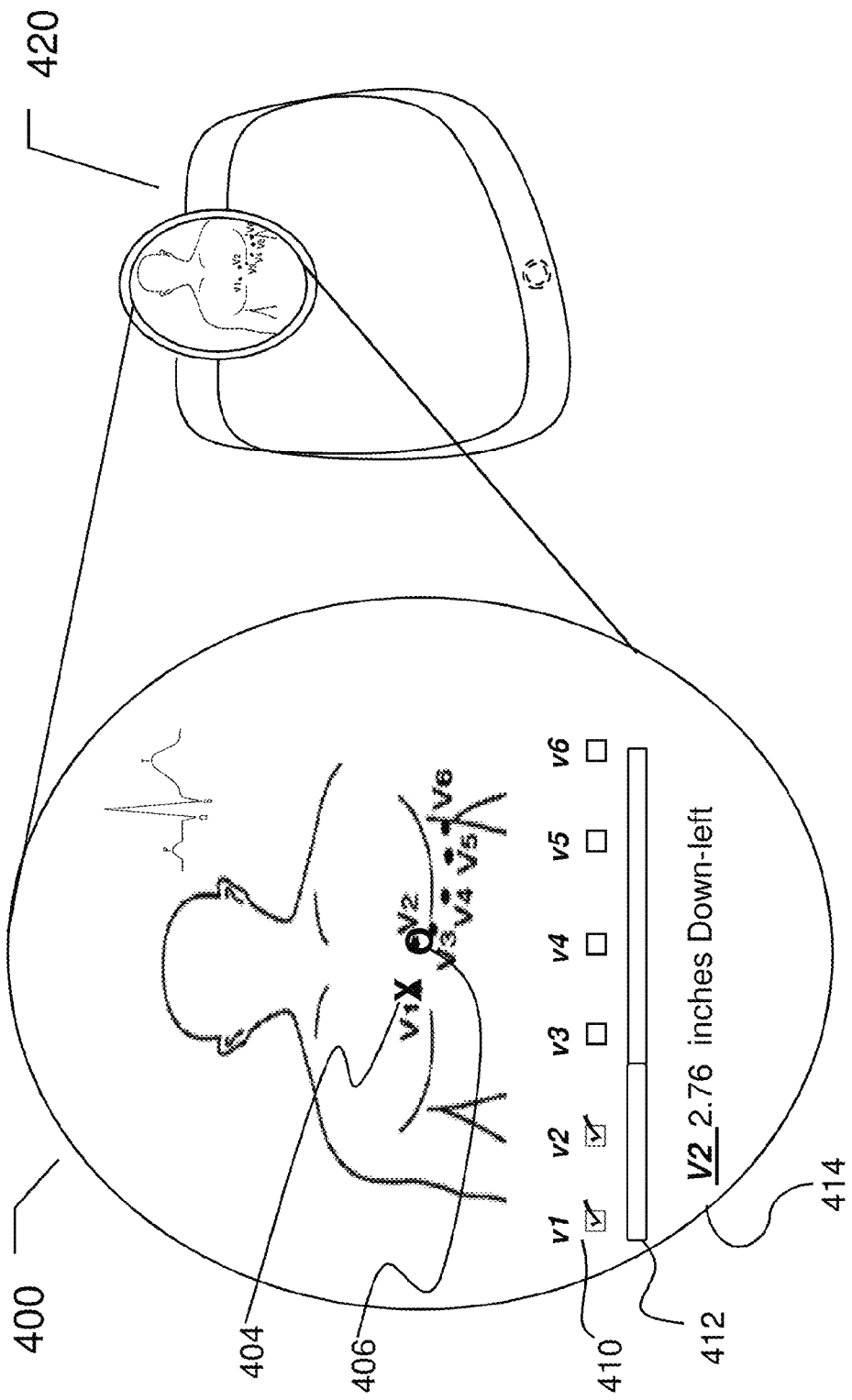

FIG. 4A depicts the use of an exemplary, illustrative guidance system according to the present invention that assists the user to find the correct recording locations, particularly on the chest and/or upper torso, preferably including recording locations V1 to V6 as depicted in FIG. 1. The navigation system of the present invention is optionally and preferably implemented for operation with the device as described in FIGS. 2A-I above. FIG. 4A relates to implementation with the device of any of FIGS. 2A-2E, while FIG. 4B relates to implementation with the device of any of FIGS. 2F-2I.

FIGS. 4A and 4B depict the use of the guidance system utilizing a platform 402 to display the guidance system to the user using a display 400. Display 400 shows an exemplary interface of the guidance system that may be optionally displayed in a plurality of platforms including the device 400 itself, and/or a separate television, mobile telephone, laptop computer, PDA, any other computer or the like, or a combination thereof.

The guidance system optionally and preferably indicates in display 400 the target location with a target symbol 406 exemplarily displayed on the figures as an 'O' (or any other symbol) which represents recording location V2 where the user is set to sample next. Similarly, the current location symbol 404 symbolized by an 'X' (or any other symbol) on the figures optionally and preferably indicates the user's current location. The current location is preferably determined by wireless communication between the device or one of its subunits (not shown) and platform 402 for example including Bluetooth, IrDA, or the like (alternatively communication may optionally be wired). Display 400 further optionally and preferably visually displays those recording locations that have already been sampled and those that have not, for example optionally both in a check box format 410 as well a progression bar 412 indicating the elapsed time from the beginning of the recording.

The guidance system optionally and preferably provides an additional indicator and instruction to the user of how to reach target location 404 by providing a text box 414 that indicates the targeted recording location as well as simple directions that optionally include the distance to the location and a relative direction such as up, down or over. Optionally verbal instructions may also be implemented with the guidance system using a loudspeaker and/or other audio device (not shown).

Figure 5B:
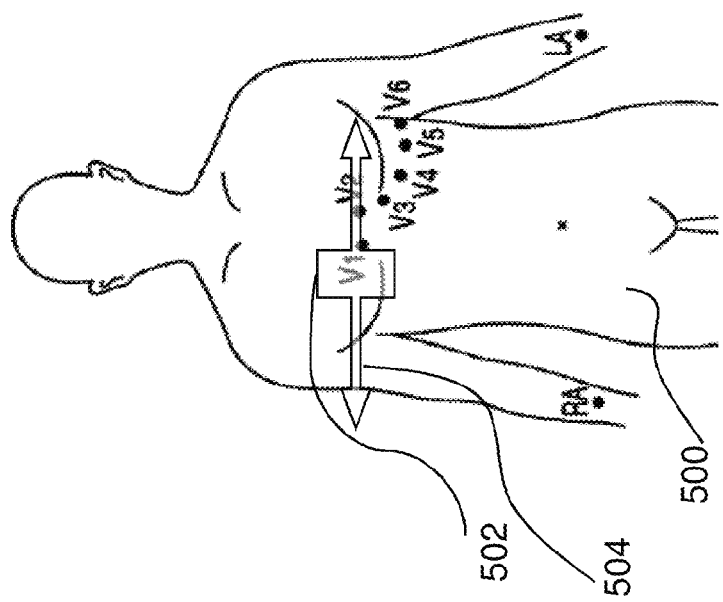
FIGS. 5A-C are an exemplary diagrammatic depiction of the optional strap utilized with the device of the present invention.

An alternative (or additional) guidance system that may optionally be used with the device of the present invention is a strap or belt that is worn on the upper torso and preferably contains predetermined recesses, holes or markings corresponding to recording locations V1 to V6. FIG. 5A depicts such a belt or strap where a recess corresponds to each recording location and may be worn about the chest. FIG. 5B depicts an alternative strap 504 that may be disposable and be coupled to device 502; strap 504 may optionally be extendible from device 502. Optionally strap 504 may be used to guide device 502 across the chest manually by user 500 or optionally automatically driven by device 502 across strap 504.

Figure 5C:
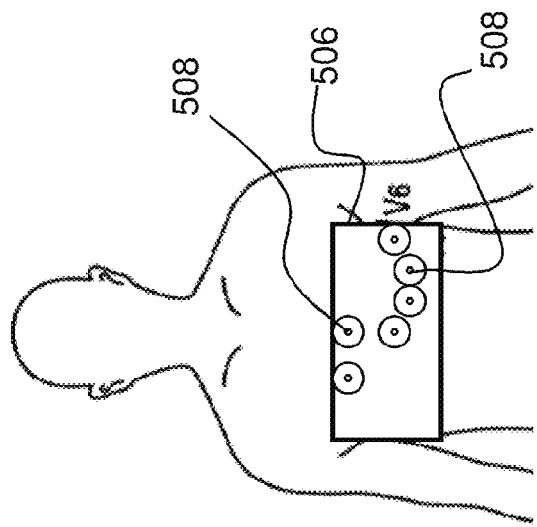
Figure 5A:
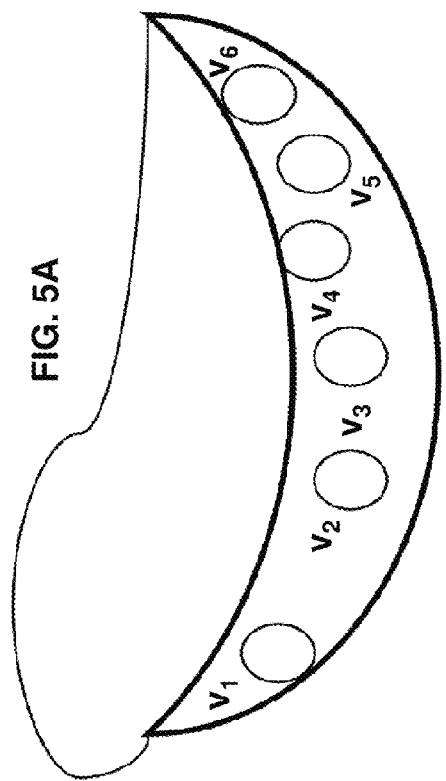

FIG. 5C shows yet another alternative strap 506 in which a plurality of electrodes 508 are embedded and/or attached to the material therein.

Figure 6:
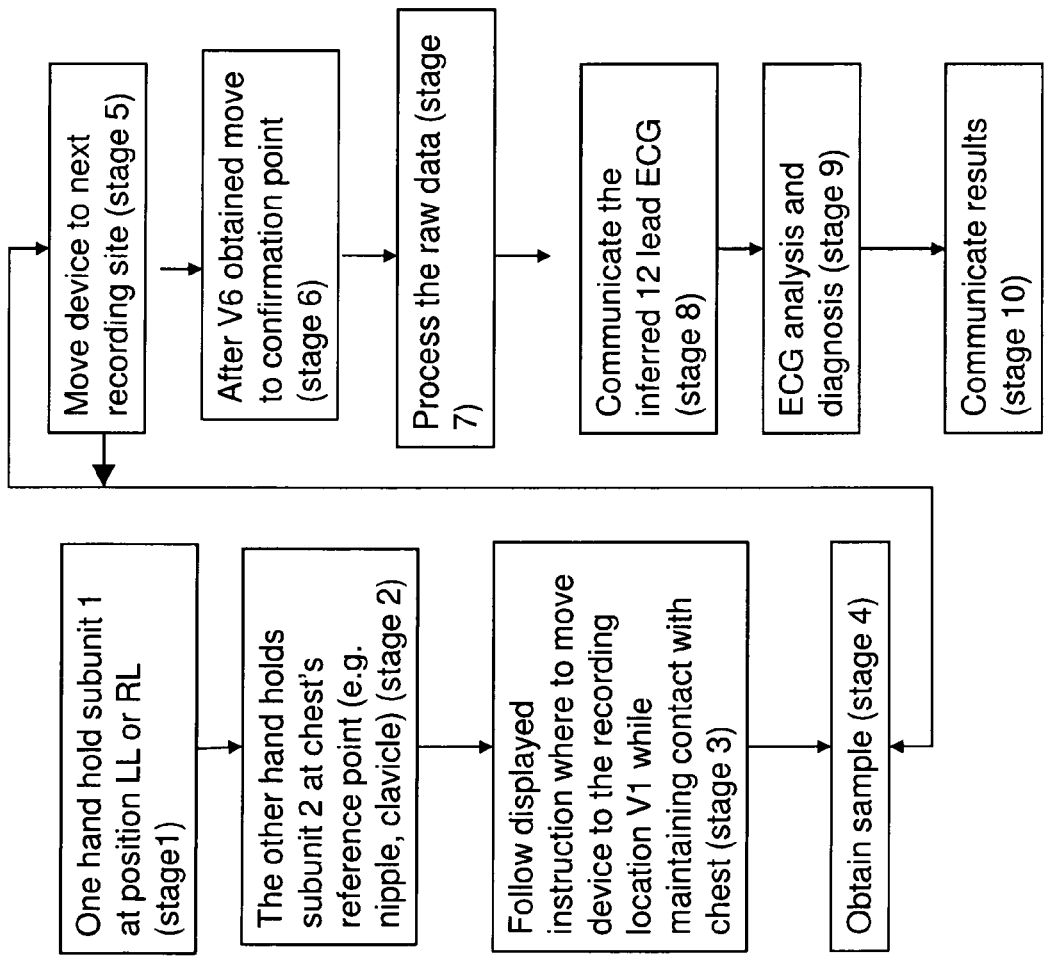
FIG. 6 is an exemplary method according to the present invention of how the ECG signal is obtained with an embodiment of the present invention.

FIG. 6 shows a flowchart of an exemplary method according to the present invention depicting the method of obtaining a 12 lead ECG signal from the 4 or 3 electrode configured device according the present invention. The current method is depicted with device 200 depicted in FIG. 2A although it may be applied to any one of the preferred embodiments of the present application. In stage 1 the first subunit 201 is held in position over recording location of the lower torso or leg. In stage 2 the second subunit 205 is placed at a reference point on the upper torso, preferably initiating navigation with the navigation system display platform. Optionally, the second unit 205 may be placed initially over the lower torso/other leg (not contacting the first subunit 201) for monitoring the limb leads before being moved to the upper torso. In stage 3 the user follows the guidance system's instructions leading the user to the first recording location V1 (in this example). In stage 4 the device begins to sample at the recording location that was reached.

In stage 5 and once the sampling ends at the current recording location the guidance system preferably guides the user to the next recording location, more preferably by repeating stages 3 and 4 until all six chest recording locations have been sampled. In stage 6, optionally the user returns the device to a confirmation point such as the reference point, as described in greater detail below. In stage 7, optionally and preferably once all of V1 to V6 recording locations have been sampled, the raw data is preferably processed by a processor either intrinsic to the device or external to construct the 12 lead ECG. In stage 8 the resultant 12 lead ECG is preferably communicated to higher processing centers for analysis. In stage 9 the higher processing center preferably performs such an analysis; it may for example be selected from the group including but not limited to a call center, a server, a decision support system, the device itself (or an external device) or a physician. In stage 10 the ECG analysis and diagnostic results are preferably communicated to the user, for example through dual communication, SMS, MMS, internet, email, facsimile, telephone call and/or other voice communication, and/or through the device itself.

Figure 7:
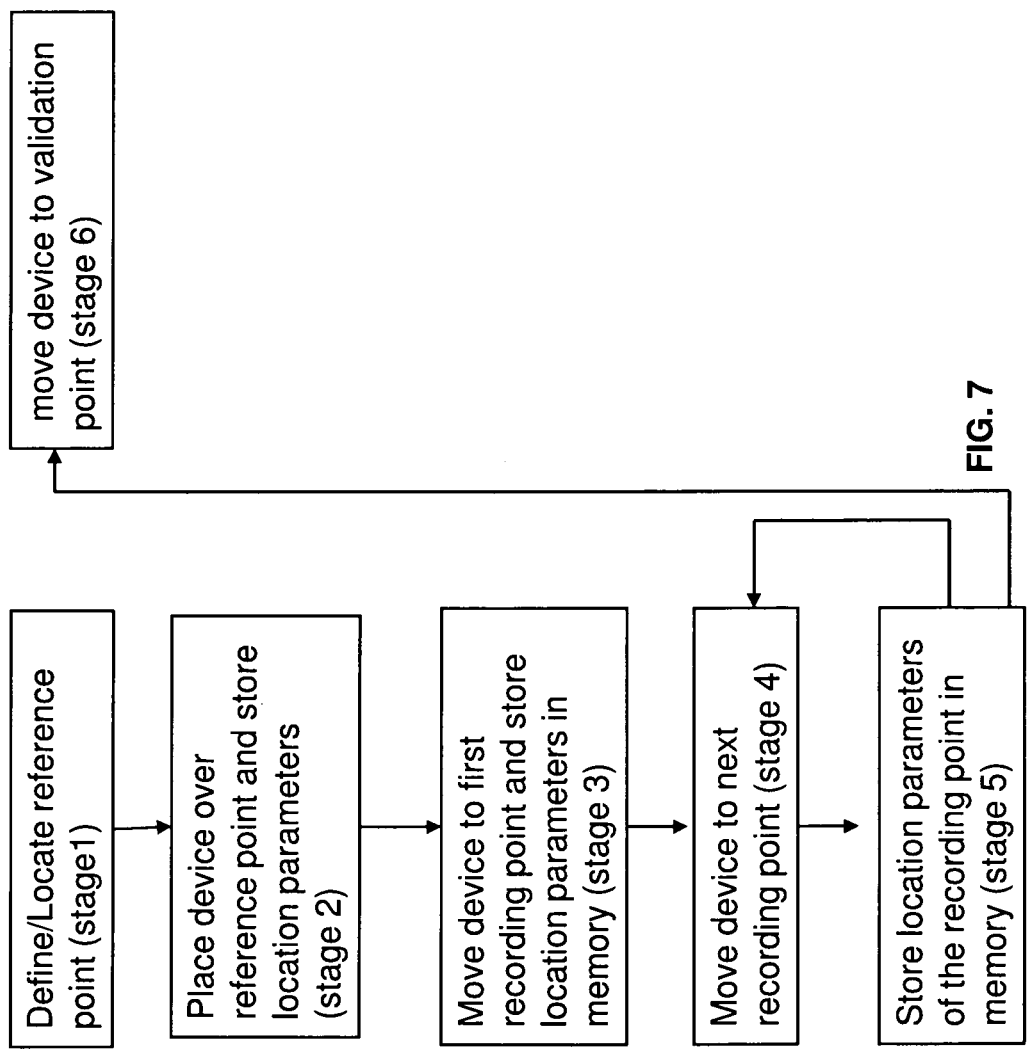
FIG. 7 shows an exemplary, illustrative embodiment of an anatomical method according to the present invention for determining a plurality of recording locations on a specific user.

FIG. 7 shows an exemplary, illustrative embodiment of an anatomical method according to the present invention for determining a plurality of recording locations on a specific user. As shown, in stage 1, a trained user preferably defines and/or locates a reference point on the specific user. In stage 2, the trained user preferably places the device over the reference point and the location parameters are stored. In stage 3, the trained user preferably moves the device to the first recording location, which is then entered to the device's memory. In stage 4, the device is preferably moved to the next recording point. In stage 5, the location parameters are stored, such that stages 4 and 5 are preferably repeated for all locations. In stage 6 the device is preferably moved to a validation point which is optionally the same initial reference point, to verify that in fact it is the same point as the initial reference point. If not then preferably a warning is given that the recording may be inaccurate. Such validation may also optionally be performed during normal operation of the device by the user.

Figure 8:
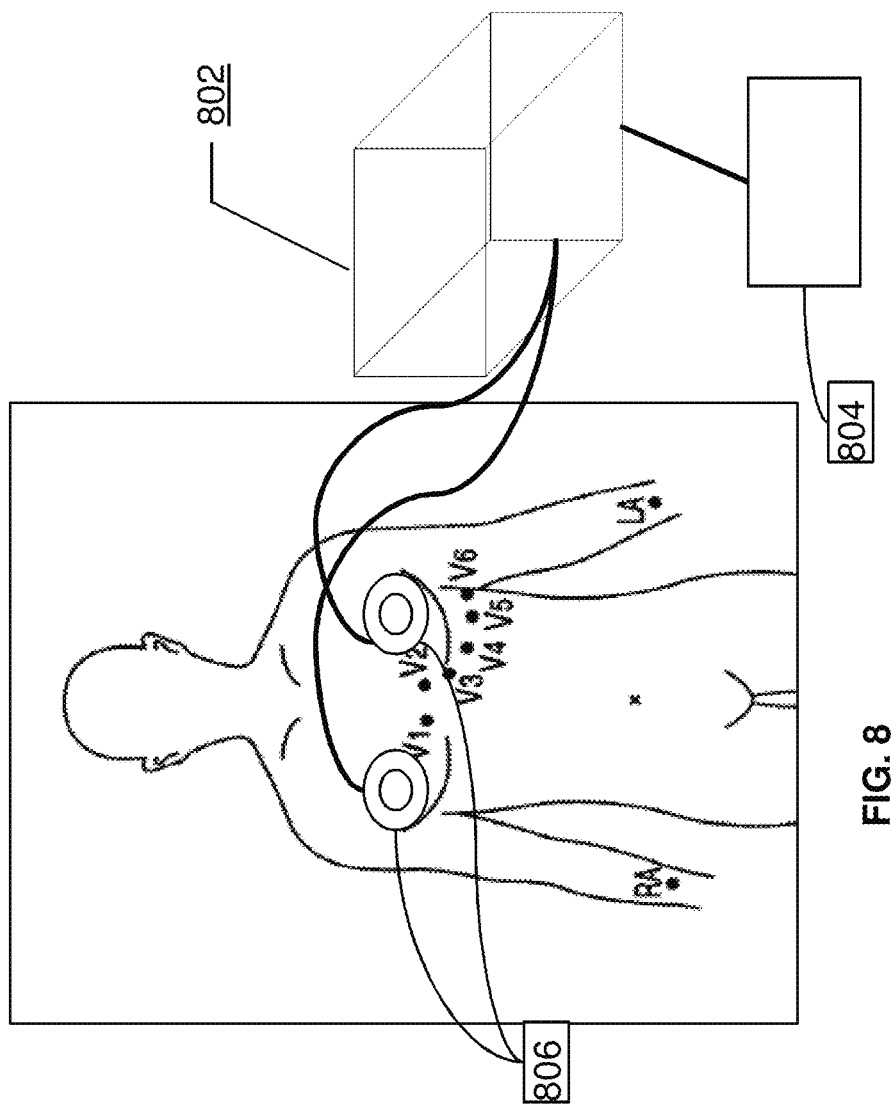
FIG. 8 shows an exemplary, illustrative personal defibrillator embodiment of the present invention.

FIG. 8 shows an exemplary, illustrative personal defibrillator embodiment of the present invention. As shown, a plurality of electrodes 806 preferably contact the skin of the chest of the subject. Electrodes 806 are preferably connected to a device 802 as described above for determining the ECG and also for determining whether a shock should be delivered through electrodes 806. An optional external power supply 804 is also shown. One electrode 806 is optionally attached (alternatively) to the back of the subject (not shown). Electrodes 806 may optionally be attached to a strap (not shown) for being held against the body of the subject.

While the invention has been described with respect to a limited number of embodiments, it will be appreciated that many variations, modifications and other applications of the invention may be made.

What is claimed is:

1. A personal ECG device for home use for deriving results of 12 lead ECG measurements by placing three electrodes on a body of a subject, comprising:
   a housing having at least two faces;
   one electrode connected to a first face of said housing adapted to record sequential measurements at 7 different locations on the body of the subject including measurements at the lower limb or lower torso of the body and at v1-v6 locations;
   two electrodes connected to at least one other face of said housing adapted to record measurements of two hands of the subject;
   a processor located within said housing configured for receiving and processing signals from the three electrodes; and
   a memory located within said housing for storing data indicative of signals measured by said three electrodes, wherein the sequential recordings at the different locations from the beginning to the end of a recording are stored in said memory,
   wherein said device is configured to allow the subject to hold said device in a manner that allows him/her to move said device over his/her body for sequentially measuring electrode signals at the 7 different locations by the first electrode connected to the first face of the housing while simultaneously allowing each hand thereof to contact a different electrode of said two electrodes that is connected to at least one other face of the housing, and
   wherein the signals sequentially recorded by the three electrodes allow said processor to derive 12 lead ECG from signal data obtained by the three electrodes during the respective recording relating to the 7 different locations and the two hands of the subject, by combining the stored recording of the measurements at the lower limb or lower torso with the measurements at the v1-v6 locations and recorded measurements of two hands of the subject acquired by the three electrodes.

2. A personal device performing conventional 12 lead ECG measurements by using four electrodes, said device comprising:
   a. a first unit having at least two faces;
   b. a second unit having at least two faces associated to the first unit by wire;
   c. a first electrode connected to a first face of the first unit adapted to record measurements at 6 different locations on the body of the subject;
   d. a second electrode connected to a first face of the second unit adapted to record measurements of at lower limb of the body or lower torso;
   e. a third electrode connected to a second face of the first unit adapted to record measurements of a first hand of the subject;
   f. a fourth electrode connected to a second face of the second unit adapted to record measurements of a second hand of the subject;
   wherein performing 12 lead ECG is done by using the first electrode that sequentially monitors and records measurements at v1-v6 locations, while the second electrode simultaneously record measurements at the lower limb or lower torso and the third and fourth electrode simultaneously record measurements at the two hands of the subject while the first electrode is recording the measurements at the V1-V6 locations such that the 12 lead EGG measurement is achieved by monitoring a total of only nine different locations using 4 electrodes.

3. The device of claim 1, wherein said processor is separate from said device.

4. The device of claim 1, wherein said processor is comprised in a computer selected from the group consisting of a cellular telephone, a laptop computer, a smartphone, a PDA and a pager.

5. The device of claim 1, further comprising a remote location for analyzing said measurements.

6. The device of claim 1, further comprising a signal amplification component.

7. The device of claim 1, further comprising a noise reduction component.

8. The device of any of claim 1, further comprising a data transmission component.

9. The device of claim 1, further comprising a navigation system for locating said plurality of different recording locations.

10. The device of claim 9, wherein said navigation system includes one or more of a visual display, an audio display or vibrating component for alerting a user as to at least one recording location.

11. The device of claim 1, further comprising a defibrillator.

12. The device of claim 1, further comprising at least one accessory selected from the group consisting of a Pulse Oximeter, stethoscope, ultrasound transducer, echocardiogram transducer, thermometer, capnograph, blood pressure cuff, fetal heart rate transducer, camera, defibrillator electrodes, wire electrodes, a carrier for a medicament and a combination thereof.

13. A method of obtaining results of 12 lead ECG data using a personal ECG device for home use by placing three electrodes on a body of a subject, comprising:
   measuring electrode signals simultaneously at a LA location on a left arm using a first electrode on a first side of the personal ECG device and a LL location on a left side torso or leg using a second electrode on a second side of the personal ECG device, measuring electrode signals simultaneously
1) at a RA location on a right arm using a third electrode on any side other than the second side of the personal ECG device, and
2) at a plurality of locations V1-V6 on the torso, by moving the device sequentially so that the second electrode connected to the second face of the device moves between the locations V1-V6 and sequentially measuring electrode signals at the V1-V6 locations, storing the measured electrode signals in a non-transitory computer readable memory, deriving, using a processor in the personal ECG device, from the stored electrode signals sequentially measured by the three electrodes, 12 lead ECG data, by combining the stored recording of the measurements at the lower limb or lower torso with the measurements at the v1-v6 locations and recorded measurements of two hands of the subject acquired by the three electrodes, and sending the 12 lead ECG data to a central location for analysis.

14. A method of obtaining results of 12 lead ECG data using a personal ECG device for home use by placing four electrodes on a body of a subject, the device comprising a first unit having at least two faces, and a second unit having at least two faces associated to the first unit by wire, the method comprising:

using a first electrode connected to a first face of the first unit that sequentially monitors and records measurements at v1-v6 locations, while simultaneously recording measurements using the second electrode at the lower limb or lower torso and simultaneously recording measurements using the third and fourth electrode at the two hands of the subject while the first electrode is recording the measurements at the V1-V6 locations such that the 12 lead EGG measurement is achieved by monitoring a total of only nine different locations using 4 electrodes.

* * * * *